United States Patent
O'Keefe

(10) Patent No.: US 11,445,669 B2
(45) Date of Patent: Sep. 20, 2022

(54) DEVICES, SYSTEMS AND METHODS FOR ENHANCED BIOMASS GROWTH IN GREENHOUSES

(71) Applicant: Carbon Sink, Inc., Cold Spring Harbor, NY (US)

(72) Inventor: Frank O'Keefe, Lloyd Neck, NY (US)

(73) Assignee: Carbon Sink Inc., Lloyd Harbor, NY (US)

( * ) Notice: Subject to any disclaimer, the term of this patent is extended or adjusted under 35 U.S.C. 154(b) by 0 days.

(21) Appl. No.: 17/029,430

(22) Filed: Sep. 23, 2020

(65) Prior Publication Data

US 2021/0084832 A1 Mar. 25, 2021

Related U.S. Application Data

(63) Continuation of application No. 15/922,017, filed on Mar. 15, 2018, now Pat. No. 10,869,430, which is a
(Continued)

(51) Int. Cl.
*A01G 9/14* (2006.01)
*A01G 7/02* (2006.01)
(Continued)

(52) U.S. Cl.
CPC ............... *A01G 9/14* (2013.01); *A01G 7/02* (2013.01); *A01G 9/18* (2013.01); *A01G 33/00* (2013.01);
(Continued)

(58) Field of Classification Search
CPC ... A01G 9/14; A01G 7/02; A01G 9/18; A01G 33/00; B01D 53/62; B01D 2253/102; B01D 2253/104; B01D 2253/108; B01D 2253/20; B01D 2257/106; B01D 2257/302; B01D 2257/304; B01D 2257/404; B01D 2257/504; B01D 2258/06; C02F 3/32;
(Continued)

(56) References Cited

U.S. PATENT DOCUMENTS 4,209,943 A 7/1980 Moeller et al.
5,197,263 A 3/1993 Midtling et al.
(Continued)

FOREIGN PATENT DOCUMENTS

CL 50674 2/2015
CL 2014002851 A1 2/2015
(Continued)

OTHER PUBLICATIONS

EP16847390.8 Extended European Search Report dated Apr. 30, 2019.
(Continued)

*Primary Examiner* — Fred Prince
(74) *Attorney, Agent, or Firm* — Whitmyer IP Group LLC

(57) ABSTRACT

Devices, systems and methods for using photosynthetic biomass to purify water, reduce indoor air pollution, remove greenhouse gases including $CO_2$ from outdoor atmospheric air, and produce biofuel, food products, and fertilizer are provided herein. Also provided herein are systems and methods for enhancing growth of a photosynthetic biomass in a greenhouse.

24 Claims, 10 Drawing Sheets

Related U.S. Application Data continuation of application No. PCT/US2016/052145, filed on Sep. 16, 2016.

(60) Provisional application No. 62/220,718, filed on Sep. 18, 2015, provisional application No. 62/318,575, filed on Apr. 5, 2016, provisional application No. 62/377,479, filed on Aug. 19, 2016.

(51) Int. Cl.

| | |
|---|---|
| *C02F 3/32* | (2006.01) |
| *A01G 9/18* | (2006.01) |
| *B01D 53/62* | (2006.01) |
| *A01G 33/00* | (2006.01) |
| *C12M 1/00* | (2006.01) |
| *C02F 103/26* | (2006.01) |

(52) U.S. Cl.
CPC ............. *B01D 53/62* (2013.01); *C02F 3/32* (2013.01); *C12M 43/06* (2013.01); *B01D 2253/102* (2013.01); *B01D 2253/104* (2013.01); *B01D 2253/108* (2013.01); *B01D 2253/20* (2013.01); *B01D 2257/106* (2013.01); *B01D 2257/302* (2013.01); *B01D 2257/304* (2013.01); *B01D 2257/404* (2013.01); *B01D 2257/504* (2013.01); *B01D 2258/06* (2013.01); *C02F 2103/26* (2013.01); *C02F 2303/04* (2013.01); *Y02C 20/40* (2020.08); *Y02P 60/20* (2015.11); *Y02W 10/37* (2015.05)

(58) Field of Classification Search
CPC . C02F 2103/26; C02F 2303/04; C12M 43/06; Y02C 20/40; Y02P 60/20; Y02W 10/37
USPC ....... 210/602, 603, 903, 747.5, 170.09, 614; 47/17
See application file for complete search history.

(56) References Cited

U.S. PATENT DOCUMENTS

| | | | |
|---|---|---|---|
| 5,636,472 A | 6/1997 | Spira et al. | |
| 7,022,223 B2 | 4/2006 | Lovestead et al. | |
| 7,655,069 B2 | 2/2010 | Wright et al. | |
| 7,708,806 B2 | 5/2010 | Wright et al. | |
| 7,790,033 B1 | 9/2010 | Debusk | |
| 7,993,432 B2 | 8/2011 | Wright et al. | |
| 8,083,836 B2 | 12/2011 | Wright et al. | |
| 8,088,197 B2 | 1/2012 | Wright et al. | |
| 8,133,305 B2 | 3/2012 | Lackner et al. | |
| 8,221,527 B1 | 7/2012 | Wright et al. | |
| 8,246,723 B2 | 8/2012 | Wright et al. | |
| 8,262,774 B2 | 9/2012 | Liu | |
| 8,273,160 B2 | 9/2012 | Wright et al. | |
| 8,337,589 B2 | 12/2012 | Wright et al. | |
| 8,715,393 B2 | 5/2014 | Wright et al. | |
| 8,999,279 B2 | 4/2015 | Wright et al. | |
| 9,205,372 B2 | 12/2015 | Wright et al. | |
| 9,266,051 B2 | 2/2016 | Wright et al. | |
| 9,266,052 B2 | 2/2016 | Wright et al. | |
| 9,527,747 B2 | 12/2016 | Wright et al. | |
| 9,616,375 B2 | 4/2017 | Wright et al. | |
| 10,869,430 B2 | 12/2020 | O'Keefe | |
| 2005/0061737 A1 | 3/2005 | Linden et al. | |
| 2009/0232861 A1 | 9/2009 | Wright et al. | |
| 2011/0195473 A1 | 8/2011 | Wilhelm | |
| 2012/0028326 A1 | 2/2012 | Jovine | |
| 2012/0117869 A1 | 5/2012 | Javan et al. | |
| 2012/0279397 A1 | 11/2012 | Wright et al. | |
| 2014/0202954 A1 | 7/2014 | Lassovsky | |
| 2014/0259997 A1* | 9/2014 | Bowling ............... | C12M 43/08 52/173.1 |
| 2014/0298717 A1 | 10/2014 | Ayers et al. | |
| 2014/0369913 A1 | 12/2014 | Nakamura et al. | |
| 2015/0237812 A1 | 8/2015 | Gupta | |

FOREIGN PATENT DOCUMENTS

| | | |
|---|---|---|
| CN | 101249368 A | 8/2008 |
| CN | 201869610 U | 6/2011 |
| CN | 103814761 A | 5/2014 |
| CN | 103947529 A | 7/2014 |
| JP | H11192498 A | 7/1999 |
| JP | 2000301192 A | 10/2000 |
| JP | 2008100178 A | 5/2008 |
| JP | 2010505613 A | 2/2010 |
| JP | 2012504942 A | 3/2012 |
| WO | WO-2008042919 A2 | 4/2008 |
| WO | WO-2009149292 A1 | 12/2009 |
| WO | WO-2008042919 A3 | 7/2010 |
| WO | WO-2017049092 A1 | 3/2017 |

OTHER PUBLICATIONS

International Search Report & Written Opinion Dec. 2, 2016 for PCT/US2016/052145.
U.S. Appl. No. 15/922,017 Office Action dated Mar. 19, 2019.
U.S. Appl. No. 15/922,017 Notice of Allowance dated Jul. 30, 2020.
U.S. Appl. No. 15/922,017 Notice of Allowance dated Nov. 16, 2020.
U.S. Appl. No. 15/922,017 Office Action dated Mar. 26, 2020.
U.S. Appl. No. 15/922,017 Office Action dated Oct. 16, 2019.
Chinese Office Action; Application No. 202110804789.6; Completed: Jul. 21, 2022; dated Jul. 28, 2022; 10 Pages.

* cited by examiner

DEVICES, SYSTEMS AND METHODS FOR ENHANCED BIOMASS GROWTH IN GREENHOUSES

CROSS-REFERENCE

This application is a Continuation of U.S. application Ser. No. 15/922,017, filed Mar. 15, 2018, which is a Continuation Application of International Patent Application No. PCT/US2016/052145, filed Sep. 16, 2016, which claims priority to U.S. Provisional Application No. 62/220,718, filed Sep. 18, 2015, U.S. Provisional Application No. 62/318,575, filed Apr. 5, 2016, and U.S. Provisional Application No. 62/377,479, filed Aug. 19, 2016, each of which is incorporated by reference herein in its entirety.

BACKGROUND

Man-made global warming and climate change are well accepted scientific facts. A well accepted cause of climate change is the excess emission of greenhouse gases such as carbon dioxide. In efforts to combat and reverse climate change, technologies have been developed to manage greenhouse gas emissions. For example, technologies have been developed to capture and store carbon dioxide from the atmosphere. Such technologies, however, are less than ideal in many cases.

Additionally, environmental health concerns posed by water pollution from sources including agricultural runoff, waste treatment, and effluent from factories, create concerns about availability of resources including arable land and clean water. Rising rates of deforestation and greenhouse-gas emissions have also had a compounded effect on the environment, creating concerns about large scale changes to weather patterns, temperatures, species extinction, and rising sea levels. Independent attempts have been made to purify water, reduce runoff, as well as capture, transport and store greenhouse gases like carbon dioxide ($CO_2$); however, these technologies are often energy inefficient and sometimes pose safety concerns.

SUMMARY OF THE INVENTION

In view of the foregoing, devices, systems and methods that combine technologies to safely address more than one environmental problem—for example water pollution and carbon capture, are needed to adequately address environmental concerns. The devices, systems and methods described herein address these concerns, and provide other advantages as well.

Recognized herein are needs to develop improved greenhouse gas capture and management devices, systems and methods. Aspects of the present disclosure provide improved devices and methods for capturing greenhouse gases such as carbon dioxide, and in other aspects utilizing such captured carbon dioxide in a secondary operation that further benefits the environment such as water purification or enhancing plant growth.

In one aspect, the present disclosure provides a system for capturing $CO_2$ from the atmosphere and treating water. In some embodiments, the system comprises an enclosure having an interior comprising one or more aquatic macrophytes, a water inlet opening in the enclosure configured to allow contaminated water to enter the enclosure and contact the aquatic macrophytes, and a solid sorbent configured to capture $CO_2$ in air exterior to the enclosure and release the captured $CO_2$ to the interior of the enclosure. In some embodiments, the aquatic macrophytes comprise *Eichhornia*, *Spirodela*, *Salvinia*, *Azolla*, *Lemna*, *Pistia*, heartleaf, or members of the duckweed family. In some embodiments, the aquatic macrophytes comprise duckweed. In some embodiments, the aquatic macrophytes consists essentially of duckweed. In some embodiments, the duckweed is of the genus *Lemna*. In any one of the preceding embodiments, the enclosure comprises a plurality of vertically arranged tiers comprising the aquatic macrophytes. In some embodiments, each tier is in fluid communication with a separate solid sorbent. In any one of the preceding embodiments, the water inlet opening is configured to allow contaminated water to enter the enclosure by having a surface of the enclosure adapted for direct contact with a surface of the contaminated water. In any one of the preceding embodiments, the system is adapted to be located outdoor such that air exterior to the enclosure is outdoor atmospheric air. In any one of the preceding embodiments, the system may also comprise an artificial light source configured to provide light to the aquatic macrophytes. In any one of the preceding embodiments, the system may also comprise a passive power source selected from the group consisting of a solar panel, a wind turbine, a hydroelectric generator, and a thermal energy converter. In any one of the preceding embodiments, the system is adapted to treat contaminated water that is a lake, a pond, a stream (e.g. waste stream), a river, a canal, or a reservoir. In any one of the preceding embodiments, the system is adapted to treat contaminated water that is agricultural runoff. In any one of the preceding embodiments, the system is adapted to treat water that contaminated with a nitrogen-containing compound. In some embodiments the nitrogen-containing compound is nitrate, nitrite, or ammonium. In any one of the preceding embodiments, the solid sorbent included in the system comprises an anion exchange material. In any one of the preceding embodiments, the system may also comprise a moisture control apparatus configured to expose the one or more solid sorbents to increased moisture that facilitates the release of $CO_2$ from the one or more solid sorbents. In any one of preceding embodiments, the moisture control apparatus comprises either a controlled water inlet configured to bring a controlled amount of water into contact with the one or more solid sorbents, or a humidifier. In any one of the preceding embodiments, the moisture control apparatus is configured to expose the one or more solid sorbents to $H_2O$ that is a gas, solid, vapor, liquid (e.g., liquid water, fine droplets as in fog, or humidity). In any one of the preceding embodiments, the solid sorbent comprises a sorbent material distributed on or in a support material. In some embodiments, the support material is a paper. In any one of the preceding embodiments, the solid sorbent is distributed about an axis around which the sorbent rotates, and the sorbent comprises a first surface and a second surface, and the solid sorbent is positioned relative to the enclosure such that as the sorbent rotates about the axis at least a portion of the first surface enters the enclosure and at least a portion of the second surface exits the enclosure. In any one of the preceding embodiments, the system may also comprise an opening in the enclosure adapted to allow treated water to exit the enclosure.

In one aspect, the present disclosure provides a method of capturing $CO_2$ from the atmosphere and treating water. In some embodiments that method comprises the steps of: (a) introducing water comprising a contaminant into an enclosure having an interior containing an aquatic macrophyte such that the water comes into contact with the aquatic macrophyte, and wherein the aquatic macrophyte facilitates the reduction of the level of the contaminant in the water; (b) capturing $CO_2$ from air exterior to the enclosure with a solid sorbent, wherein air exterior to the enclosure has a $CO_2$ concentration of less than 800 ppm; and (c) releasing captured $CO_2$ into the interior of the enclosure, wherein the interior of the enclosure has a higher $CO_2$ concentration than the air exterior to the enclosure. In some embodiments, the aquatic macrophytes used in the method comprise *Eichhornia, Spirodela, Salvinia, Azolla, Lemna, Pistia*, heartleaf or members of the duckweed family. In some embodiments, the aquatic macrophyte comprises duckweed. In some embodiments, the aquatic macrophyte consists essentially of duckweed. In any one of the preceding embodiments, the duckweed is of the genus *Lemna*. In any one of the preceding embodiments, the enclosure comprises a plurality of vertically arranged tiers comprising the aquatic macrophytes. In any one of the preceding embodiments, the method uses a system wherein each tier is in fluid communication with a separate solid sorbent. In any one of the preceding embodiments, a surface of the enclosure is in direct contact with a surface of the body of water. In any one of the preceding embodiments, the air exterior to the enclosure is outdoor atmospheric air. In any one of the preceding embodiments, the method uses a system that further comprises an artificial light source. In any one of the preceding embodiments, a power source supplies power to the enclosure. In some embodiments, the power source is selected from the group comprising a solar panel, a wind turbine, a hydroelectric generator, and a thermal energy converter. In any one of the preceding embodiments, the body of water is a lake, a pond, a stream, a river, a canal, or a reservoir. In any one of the preceding embodiments, the body of water is agricultural runoff. In any one of the preceding embodiments, the water is contaminated with a nitrogen-containing compound. In any one of the preceding embodiments, the water is contaminated with a nitrogen-containing compound comprising nitrate, nitrite, or ammonium. In any one of the preceding embodiments, the solid sorbent comprises an anion exchange material. In any one of the preceding embodiments, the step of releasing captured $CO_2$ comprises wetting the sorbent or exposing the sorbent to increased humidity. In any one of the preceding embodiments, the solid sorbent comprises a sorbent material distributed on or in a support material. In any one of the preceding embodiments, the solid sorbent comprises a sorbent material distributed on or in a paper. In any one of the preceding embodiments, the solid sorbent is distributed about an axis around which the sorbent rotates, and the sorbent comprises a first surface and a second surface, and the solid sorbent is positioned relative to the enclosure such that as the sorbent rotates about the axis at least a portion of the first surface enters the enclosure and at least a portion of the second surface exits the enclosure, and wherein the method further comprises rotating the sorbent about the axis to alternate exposing the first surface and the second surface to the exterior of the enclosure. In any one of the preceding embodiments, the enclosure further comprises an opening through which purified water exits the enclosure. In any one of the preceding embodiments, the contaminant in the treated water exiting the enclosure has a concentration that is at least 10% lower as compared to the water entering the enclosure. In any one of the preceding embodiments, the method may also comprise the step of maintaining the $CO_2$ concentration in the interior of the enclosure at a level at which the aquatic macrophyte exhibits a growth rate or reproduction rate that is at least 2-fold increased as compared to growth or reproduction of the aquatic macrophyte in the air exterior to the enclosure. In any one of the preceding embodiments, the method may also comprise the step of maintaining the $CO_2$ concentration in the interior of the enclosure at a level at which the duckweed exhibits a growth rate or reproduction rate that is at least 2-fold increased as compared to growth or reproduction of the duckweed in the air exterior to the enclosure. In any one of the preceding embodiments, a desired $CO_2$ concentration is maintained in the interior containing the aquatic macrophyte for at least 2 days, or at least 3 days, or at least 4 days, or at least 5 days, or at least 7 days, or at least 10 days, or at least 14 days, or at least 30 days. In any one of the preceding embodiments, the growth or reproduction rate of the duckweed is at least 8-fold increased as compared to the growth or reproduction rate of duckweed in an environment containing about 400 ppm $CO_2$ or less. In any one of the preceding embodiments, the method may also comprise the step of maintaining the $CO_2$ concentration in the interior of the enclosure at a concentration of at least 1000 ppm, 1200 ppm, 1500 ppm, or higher. In any one of the preceding embodiments, the $CO_2$ concentration in the interior is maintained at a desired $CO_2$ concentration at for at least 2 days, or at least 3 days, or at least 4 days, or at least 5 days, or at least 7 days, or at least 10 days, or at least 14 days, or at least 30 days. In any one of the preceding embodiments, the method may also comprise harvesting the duckweed. In any one of the preceding embodiments, the method may also comprise continuously harvesting the duckweed for an extended period of time (e.g., a day, a week, or a month). In some embodiments, the harvesting is performed by a floating an automated device. In any one of the preceding embodiments, the method may also comprise collecting oil from the duckweed. In any one of the preceding embodiments, the method may also comprise collecting oil from the duckweed by one or more of pressing or boiling the duckweed. In any one of the preceding embodiments, the method may also comprise producing a fuel, such as a biodiesel, from oil collected from the duckweed. In any one of the preceding embodiments, the method may also comprise using the duckweed in the production of a commercial product. In any one of the preceding embodiments, the method may also comprise using the duckweed in the production of a commercial product comprising a fuel, a food product, starch or a fertilizer. In any one of the preceding embodiments, the method may also comprise using the duckweed in the production of a commercial product comprising a food product that is animal feed.

In one aspect, the present disclosure provides a system for enhancing plant growth comprising: (a) an enclosure comprising a plurality of compartments, wherein at least one first compartment comprises a growing photosynthetic biomass and at least one second compartment is adapted to accommodate one or more mammals that exhale $CO_2$ into air of the at least one second compartment; (b) one or more solid sorbents in fluid communication with the at least one second compartment, wherein the one or more solid sorbents are configured to capture $CO_2$ in the air of the at least one second compartment; (c) moisture control apparatus configured to expose the one or more solid sorbents to increased moisture that facilitates the release of $CO_2$ therefrom; and (d) one or more conduits fluidically connecting the one or more solid sorbents and the at least one first compartment such that the one or more conduits are configured to facilitate the delivery of $CO_2$ released from the one or more solid sorbents to the at least one first compartment. In some embodiments, the moister control apparatus comprises apparatus adapted to bring water into contact with the one or more solid sorbents or apparatus adapted to increase the humidity exposed to the one or more solid sorbents. In any one of the preceding embodiments, the moisture control apparatus comprises either (1) a controlled water inlet configured to bring a controlled amount of water into contact with the one or more solid sorbents, or (2) a humidifier. In any one of the preceding embodiments, the moisture control apparatus is configured to expose the one or more solid sorbents to $H_2O$ that is a gas, vapor, solid, or liquid. In any one of the preceding embodiments, the moisture control apparatus comprises one or more stores of water and one or more dispensers that deliver water in liquid or vapor form to the one or more solid sorbents. In any one of the preceding embodiments, at least one second compartment is adapted to be habitable by humans. In any one of the preceding embodiments, the system may also comprise a growth tent that houses the photosynthetic biomass. In any one of the preceding embodiments, the at least one first compartment is located below the at least one second compartment. In any one of the preceding embodiments, the system may also comprise a control mechanism adapted to maintain the $CO_2$ level in the at least one second compartment below 500 ppm. In any one of the preceding embodiments, the system may also comprise a system control mechanism that comprises one or more sensors or detectors and a processor, wherein the one or more sensors or detectors are configured to provide information to the processor, and the processor is configured to use such information to determine either or both (1) an appropriate rotation rate of the sorbent, or (2) the amount of moisture to which the one or more sorbents is exposed, in order to achieve a desired $CO_2$ level in one of the plurality of compartments. In any one of the preceding embodiments, the system may also comprise an air control system that regulates the flow of air. In any one of the preceding embodiments, the sensors or detectors comprise mechanisms for detecting the time of day, motion of mammals or occupants, quantity of mammals or occupants, humidity in one or more ambient compartments. In any one of the preceding embodiments, the system may also comprise a system control mechanism adapted to maintain the $CO_2$ level in the at least one first compartment above 500 ppm. In any one of the preceding embodiments, the system control mechanism is configured for using feedback from one or more sensors or detectors to determine the rotation rate of the sorbent. In any one of the preceding embodiments, the system control mechanisms is configured for detecting or controlling one or more environmental conditions of the one or more greenhouse compartments. In any one of the preceding embodiments, the system control mechanisms is configured for detecting or controlling one or more environmental conditions that may include temperature, light, water, nutrient levels, humidity levels, $CO_2$ levels in one or more greenhouse compartments. In any one of the preceding embodiments, the photosynthetic biomass is an edible plant. In any one of the preceding embodiments, the one or more sorbents are installed downstream of an intake for a forced-air system for regulating temperature in the at least one second compartment. In any one of the preceding embodiments, the system may also comprise an artificial light source to which the photosynthetic biomass is exposed. In any one of the preceding embodiments, the one or more solid sorbents comprise an anion exchange material. In any one of the preceding embodiments, the one or more solid sorbents comprise a sorbent material distributed on or in a support material. In any one of the preceding embodiments, the one or more solid sorbents comprise a sorbent material distributed on or in a support material that is a paper for example a synthetic paper.

In one aspect, the present disclosure provides a method of enhancing growth of a photosynthetic biomass comprising: (a) providing an enclosure having at least one first compartment containing the photosynthetic biomass, and at least one second compartment that is habitable; (b) capturing $CO_2$ exhaled into air from the at least one second compartment with one or more solid sorbents, wherein $CO_2$ in the at least one second compartment is maintained below 0.5%; (c) exposing the solid sorbent to moisture thereby releasing captured $CO_2$; (d) transferring the released $CO_2$ to the at least one first compartment, wherein $CO_2$ in the at least one first compartment is maintained at a higher concentration than in the at least one second compartment for an extended period of time. In some embodiments, the photosynthetic biomass comprises *Eichhornia, Spirodela, Salvinia, Azolla, Lemna, Pistia*, heartleaf, or members of the duckweed family. In any one of the preceding embodiments, the $CO_2$ concentration in the at least one first compartment is maintained at a higher concentration than in the $CO_2$ concentration in the at least one second compartment for at least 2 days, or at least 3 days, or at least 4 days, or at least 5 days, or at least 7 days, or at least 10 days, or at least 14 days, or at least 30 days. In any one of the preceding embodiments, the photosynthetic biomass is contained in a growth tent. In any one of the preceding embodiments, the at least one first compartment is located below the at least one second compartment. In any one of the preceding embodiments, $CO_2$ in the at least one second compartment is maintained below 500 ppm. In any one of the preceding embodiments, $CO_2$ in the at least one first compartment is maintained above 500 ppm. In any one of the preceding embodiments, the photosynthetic biomass is an edible plant. In any one of the preceding embodiments, the one or more sorbents are installed downstream of an intake for a forced-air system for regulating temperature in the at least one second compartment, and capturing $CO_2$ comprises drawing air past the one or more solid sorbents. In any one of the preceding embodiments, the photosynthetic biomass is exposed to an artificial light source. In any one of the preceding embodiments, the one or more solid sorbents comprise an anion exchange material. In any one of the preceding embodiments, the one or more solid sorbents comprise a sorbent material distributed on or in a support material. In any one of the preceding embodiments, the one or more solid sorbents comprise a sorbent material distributed on or in a support material that is a paper. In any one of the preceding embodiments, the step of exposing the solid sorbent to moisture comprises exposing the solid sorbent to $H_2O$ that is a gas, solid, or liquid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
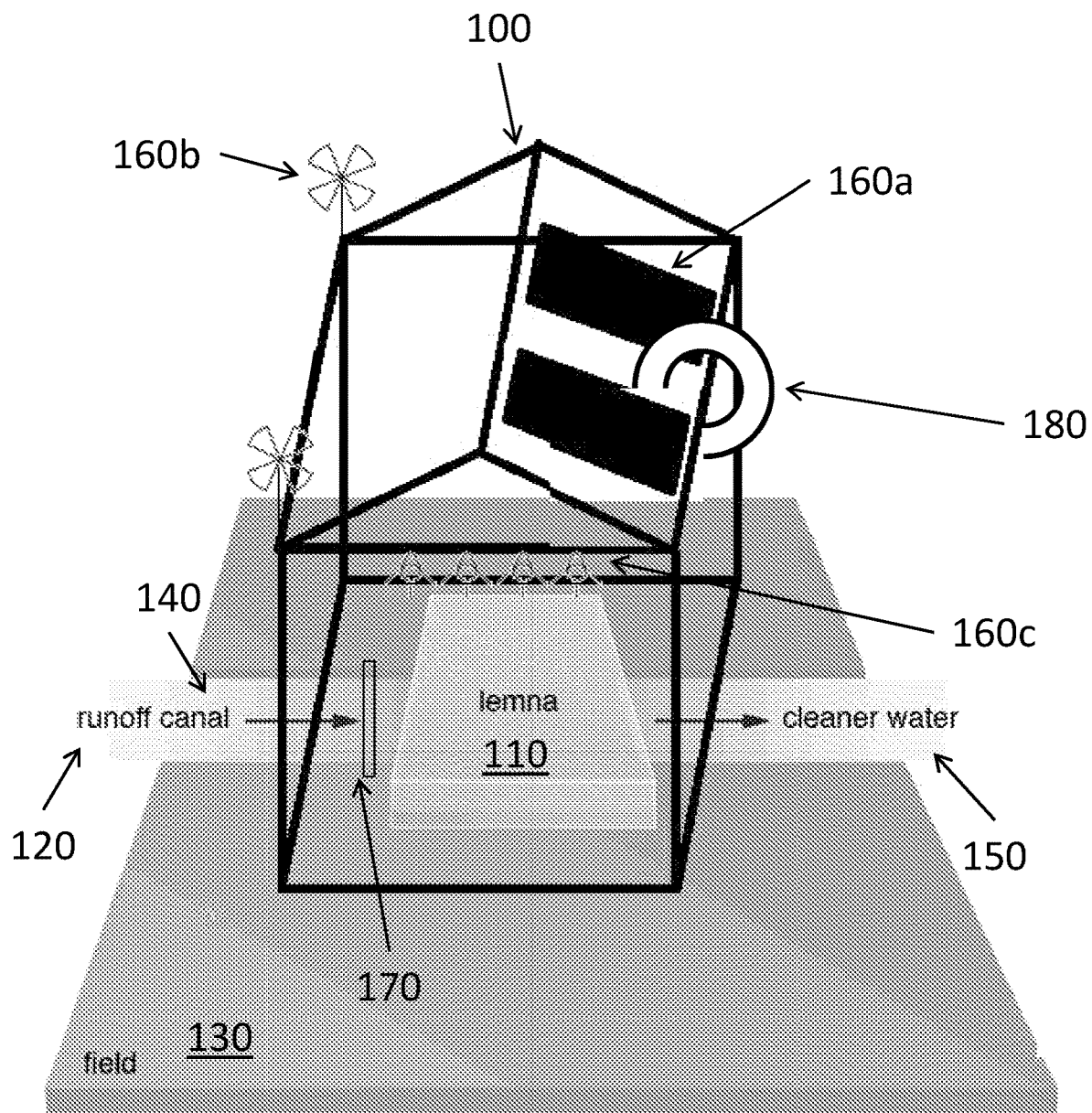
FIG. 1 shows a schematic of a system for purifying water, in accordance with an embodiment.

In one aspect, the present disclosure provides a system for either or both purifying water and/or capturing $CO_2$ from the atmosphere. In some embodiments the system comprises duckweed, a floating aquatic plant or macrophyte known in the art for facilitating the degradation of organic material in shallow water environments. It is well known in the art that floating duckweed together with attached bacteria and algae, form a mat on the water surface that facilitates degradation of organic material through various means including through enrichment of oxygen supply and by providing additional surface for growth of nitrogen fixing bacteria. In some embodiments, the system comprises (a) an enclosure having a water purification apparatus comprising (i) an interior within the enclosure that contains a duckweed; and (ii) a water inlet opening and a water outlet opening in the enclosure through which water from a body of water containing a contaminant enters and exits the enclosure such that the water comes into contact with the duckweed, thereby reducing the concentration of the contaminate within the water; and (b) a carbon capture apparatus comprising a solid sorbent that captures $CO_2$ from an air source and releases captured $CO_2$ to the interior of the enclosure, wherein the sorbent is in fluid communication with the interior of the enclosure, and as the system operates the air in the interior of the enclosure achieves a higher $CO_2$ concentration than the air source. In some embodiments, the enclosure comprises a plurality of vertically arranged tiers comprising the duckweed. In some embodiments, each tier is in fluid communication with a separate solid sorbent. In some embodiments, a surface of the enclosure is in direct contact with a surface of the body of water. In some embodiments, the air source comprises air that is exterior to the enclosure and is outdoor atmospheric air. In some embodiments, the air source has a $CO_2$ concentration of less than 800 ppm. In some embodiments, the duckweed is of the genus *Lemna*. In some embodiments, the system further comprises an artificial light source, such as LED lighting. In some embodiments, the system further comprises a passive power source, such as a power source selected from the group consisting of: a solar panel, a wind turbine, a hydroelectric generator (e.g. tidal power, wave power, or hydro-turbines), and a thermal energy converter (e.g. ocean thermal energy). In some embodiments, the body of water is a lake, a pond, a stream (e.g. a waste stream), a river, a canal, or a reservoir. In some embodiments, the body of water is agricultural runoff. In some embodiments, the contaminant is a nitrogen-containing compound, such as nitrate, nitrite, or ammonium. In some embodiments, the contaminant is phosphorous. In some embodiments, the solid sorbent comprises an anion exchange material. In some embodiments, the system is used in a method that comprises exposing the sorbent to moisture (e.g., water or increased humidity) and thereby causing the $CO_2$ captured by the sorbent to be released. In some embodiments, the sorbent releases captured $CO_2$ upon wetting or exposure to increased humidity. In some embodiments, the solid sorbent comprises a sorbent material distributed on or in a support material, such as a material formed into a sheet (e.g. paper). In some embodiments, the system is used in a method that comprises periodically repositioning the sorbent such that at a first sorbent position a first surface of the sorbent is exposed to the air source and a second surface of the sorbent is exposed to the interior of the enclosure, and at a second sorbent position the first surface of the sorbent is exposed to the interior of the enclosure (or isolated from both the interior and exterior of the enclosure) and the second surface of the sorbent is exposed to the air source (or isolated from both the interior and exterior of the enclosure). In some embodiments, the solid sorbent is distributed about an axis around which the sorbent rotates, and the method of periodically repositioning the sorbent comprises rotating the sorbent about such axis. In some embodiments, the contaminant in water exiting the enclosure has a concentration that is at least 10% lower as compared to water entering the enclosure (e.g. at least 15%, 25%, 50%, 75%, or 90% lower). In some embodiments, $CO_2$ concentration in the interior of the enclosure is maintained at a level at which the duckweed exhibits a growth rate that is at least 2-fold increased as compared to growth of the duckweed in the air exterior to the enclosure (e.g. at least 4-fold, 6-fold, 8-fold, 10-fold, 15-fold, or 20-fold). In some embodiments such enhanced growth rate is observed every 24 to 48 hours. In some embodiments such enhanced growth rate is observed every 24 to 36 hours. In some embodiments, air in the interior of the enclosure has a $CO_2$ concentration of at least 1000 ppm, 1200 ppm, 1500 ppm, or higher. In some embodiments above-described enhanced growth rate occurs at a $CO_2$ concentration of at least 1000 ppm, 1200 ppm, 1500 ppm, or higher.

The term "about" may be used herein to refer to an approximate range around some defined quantity or to indicate that a mechanical structure moves along or is oriented proximate to a nearby physical entity. In instances when the term "about" is used to refer to a range around a defined quantity, the term may be defined as within a range of 10% greater than or 10% less than the defined quantity.

In one aspect, the present disclosure provides a method of purifying water. That method may also provide for simultaneously capturing $CO_2$ from the atmosphere. In some embodiments, the method comprises: (a) introducing water comprising a contaminant into an enclosure having an interior containing a duckweed, wherein the duckweed removes the contaminant from the water; (b) capturing $CO_2$ from air exterior to the enclosure with a solid sorbent and (c) releasing captured $CO_2$ into the interior of the enclosure, wherein the interior of the enclosure has a higher $CO_2$ concentration than the air exterior to the enclosure. In some embodiments, the air exterior to the enclosure has a $CO_2$ concentration of less than 800 ppm. In some embodiments, the enclosure comprises a plurality of vertically arranged tiers comprising the duckweed. In some embodiments, each tier is in fluid communication with a separate solid sorbent. In some embodiments, a surface of the enclosure is in direct contact with a surface of the body of water. In some embodiments, the air exterior to the enclosure is outdoor atmospheric air. In some embodiments, the duckweed is of the genus *Lemna*. In some embodiments, the enclosure further comprises an artificial light source, such as LED lighting. In some embodiments, a passive power source supplies power to the enclosure. Non-limiting examples of passive power sources include solar panels, wind turbines, hydroelectric generators (e.g. tidal power, wave power, and hydro-turbines), and thermal energy converters (e.g. ocean thermal energy). In some embodiments, the body of water is a lake, a pond, a stream, a river, a canal, or a reservoir. In some embodiments, the body of water is agricultural runoff. In some embodiments, the contaminant is a nitrogen-containing compound, such as nitrate, nitrite, or ammonium. In some embodiments, the solid sorbent comprises an anion exchange material. In some embodiments, the solid sorbent comprises a sorbent material distributed on or in a support material, such as a material formed into a sheet or deposited on paper. In some embodiments, the method further comprises periodically repositioning the solid sorbent such that a surface on the sorbent alternates between fluid communication with the interior of the enclosure and fluid communication with the exterior of the enclosure. In some embodiments, wherein (i) the solid sorbent is distributed about an axis around which the sorbent rotates; and (ii) the sorbent comprises an exterior surface exposed to the exterior of the enclosure and an interior surface exposed to the interior of the enclosure; the method further comprises rotating the sorbent about the axis such that at least a portion of the exterior surface enters the enclosure and at least a portion of the interior surface exits the enclosure. In some embodiments, the enclosure further comprises an opening through which purified water exits the enclosure. In some embodiments, the contaminant in water exiting the enclosure has a concentration that is at least 10% lower as compared to water entering the enclosure (e.g. at least 15%, 25%, 50%, 75%, or 90% lower). In some embodiments, the method further comprises regulating the $CO_2$ concentration in the interior of the enclosure. In some embodiments, the $CO_2$ concentration in the interior of the enclosure is regulated by regulating the rate at which a surface of the solid sorbent is periodically repositioned to alternate between fluid communication with the interior of the enclosure and fluid communication with the exterior of the enclosure. In some embodiments, $CO_2$ concentration in the interior of the enclosure is maintained at a level at which the duckweed exhibits a growth rate that is at least 2-fold increased as compared to growth of the duckweed in the air exterior to the enclosure (e.g. at least 4-fold, 6-fold, 8-fold, 10-fold, 15-fold, or 20-fold). In some embodiments, air in the interior of the enclosure has a $CO_2$ concentration of at least 1000 ppm, 1200 ppm, 1500 ppm, or higher. In some embodiments, the method further comprises harvesting the duckweed, such as harvesting continuously. In some embodiments, harvesting is performed by a floating automated device. In some embodiments, the method further comprises utilizing the duckweed to make a commercial product. In some embodiments, the method further comprises collecting oil from the duckweed, such as by pressing and/or boiling the harvested duckweed. In some embodiments, the method further comprises producing a commercial product from the duckweed oil, and in some embodiments that product is a fuel, such as a biodiesel. In some embodiments, the method further comprises using the duckweed in the production of a commercial product that is a food product (e.g. animal feed), starch or fertilizer.

In one aspect, the disclosure provides a system for enhancing plant growth. In some embodiments, the system comprises: (a) a habitable enclosure comprising a plurality of compartments separated by a plurality of partitions, wherein at least one first compartment contains a growing photosynthetic biomass and at least one second compartment contains one or more mammals that exhale $CO_2$ into the air of the at least one such second compartment; (b) one or more solid sorbents in fluid communication with the air or water of at least one first compartment and the air or water of at least one second compartment, wherein (i) the one or more solid sorbents is operably configured to capture $CO_2$ from the air of such second compartment, such that the air of such second compartment is maintained at a preferred $CO_2$ concentration (e.g., about 1% or less); and (ii) the one or more solid sorbents is operably configured to release $CO_2$ into the air or water of such first compartment such that the $CO_2$ concentration in air in such first compartment is maintained at a level that is higher than the $CO_2$ concentration in the air or water of at least one second compartment. In one aspect, the system may further include a moisture source capable of selectively providing moisture to the solid sorbent thereby causing the release of captured $CO_2$. The moisture source may provide moisture in any state, such as by wetting with liquid water or by exposure to increased humidity. In some embodiments, the one or more mammals are humans. In some embodiments, the photosynthetic biomass is contained in or the first compartment comprises a growth tent. In some embodiments, the system further comprises one or more stores of water and one or more dispensers that deliver water in liquid or vapor form to the one or more solid sorbents. In some embodiments, the at least one first compartment is located below the at least one second compartment. In some embodiments, $CO_2$ in the at least one second compartment is maintained below 1000 ppm (e.g. below 500 ppm). In some embodiments, $CO_2$ in the at least one first compartment is maintained above 500 ppm (e.g. above 600 ppm, 800 ppm, 900 ppm, 1000 ppm, 1200 ppm, 1500 ppm, or 2000 ppm). In some embodiments, the photosynthetic biomass is an edible plant. In some embodiments, the one or more sorbents are installed downstream of an intake for a forced-air system, such as a system for regulating temperature or humidity in the at least one second compartment. In some embodiments, the system further comprises an artificial light source to which the photosynthetic biomass is exposed. In some embodiments, the one or more solid sorbents comprise an anion exchange material. In some embodiments, the one or more solid sorbents comprise a sorbent material distributed on or in a support material, such as a material formed as a sheet (e.g. a paper).

In one aspect, the present disclosure provides a method of enhancing growth of a photosynthetic biomass in at least one first compartment of an enclosure that also includes at least one habitable second compartment. In some embodiments, the method comprises: (a) capturing $CO_2$ (e.g. exhaled $CO_2$) from air of at least one second compartment of the enclosure with one or more solid sorbents, wherein $CO_2$ in the at least one second compartment is maintained below a preferred level (e.g. below 1%, below 0.5%, below 2000 ppm, 1000 ppm, or 500 ppm); and (b) exposing the one or more solid sorbents to moisture by wetting or increased exposure to humidity thereby releasing the captured $CO_2$ into the at least one first compartment comprising the photosynthetic biomass, wherein the $CO_2$ in the at least one first compartment is maintained at a higher concentration than the $CO_2$ in the at least one second compartment. In some further embodiments the solid sorbent releases captured $CO_2$ upon wetting or exposure to increased humidity. In some embodiments, the photosynthetic biomass is contained in or the first compartment comprises a growth tent. In some embodiments, the at least one first compartment is located below the at least one second compartment. In some embodiments, $CO_2$ in the at least one second compartment is maintained below 1000 ppm (e.g. below 500 ppm). In some embodiments, $CO_2$ in the at least one first compartment is maintained above 500 ppm (e.g. above 600 ppm, 800 ppm, 900 ppm, 1000 ppm, 1200 ppm, 1500 ppm, or 2000 ppm). In some embodiments, the photosynthetic biomass is an edible plant. In some embodiments, the one or more sorbents are installed downstream of an intake for a forced-air system (e.g. a system for regulating temperature or humidity in the at least one second compartment), and capturing $CO_2$ comprises drawing air past the one or more solid sorbents. In some embodiments, the photosynthetic biomass is exposed to an artificial light source. In some embodiments, the one or more solid sorbents comprise an anion exchange material. In some embodiments, the one or more solid sorbents comprise a sorbent material distributed on or in a support material, such as a paper.

In one aspect, the present disclosure provides a device for sequestering a greenhouse gas. In many embodiments, the device comprises a housing, a sorbent, and a motor. The housing is divided into first and second compartments. The sorbent is disposed within the housing and has first and second portions which alternate between exposure to the first and second compartments of the housing. The sorbent absorbs the greenhouse gas when exposed in the first compartment and releases the greenhouse gas when exposed to the second compartment. The motor is coupled to the sorbent to actuate the sorbent to alternate the exposure of the first and second portions to the first and second compartments of the housing. In some embodiments the sorbent includes multiple portions that alternate among exposure of the first compartment, isolation from the first and second compartment, and exposure to the second compartment. In some embodiments, the first compartment of the housing comprises a first inlet and a first outlet both open to a first air environment, the second compartment of the housing comprises a second inlet and a second outlet open to a second air environment, and the first air environment has a lesser concentration of the greenhouse gas than the second air environment. In some embodiments, one or more of the first inlet, the first outlet, the second inlet, or the second outlet comprise a fan to facilitate air circulation. In some embodiments, the first air environment comprises ambient air. In some embodiments, the second air environment comprises an interior of a greenhouse. In some embodiments, the first air environment has a lesser humidity than the second air environment. In some embodiments, the absolute humidity of the first air environment or first compartment is less than about 1 gram per $m^3$, less than about 2.5 grams/$m^3$, less than about 5 grams/$m^3$, less than about 10 grams/$m^3$, less than about 15 grams/$m^3$, or less than about 20 grams/$m^3$. In some embodiments, the first compartment of the housing comprises air with a lesser humidity than in the second compartment. In some embodiments, the sorbent is configured to absorb the greenhouse gas in a low humidity environment and release the greenhouse gas in a high humidity environment. In some embodiments, the absolute humidity of the second air environment or second compartment is greater than about 25 g/$m^3$, greater than about 20 grams/$m^3$, greater than about 15 grams/$m^3$, greater than about 10 grams/$m^3$, or greater than about 5 grams/$m^3$. In some embodiments, the greenhouse gas comprises carbon dioxide. In some embodiments, the motor comprises a rotary motor. In some embodiments, the device further comprises a spinning element housing the sorbent and coupled to the motor. The rotary motor is coupled to the spinning element to alternate portions of the spinning element between exposure in the first and second compartments of the housing. In some embodiments, the spinning element comprises a spinning wheel. In some embodiments, the sorbent in the spinning element is housed in a plurality of segments isolated from one another.

In one aspect, the present disclosure provides a method for sequestering a greenhouse gas. In many embodiments, the method comprises the steps of (a) exposing a first portion of a sorbent to a first air environment to absorb the greenhouse gas therein, while a second portion of the sorbent is isolated from the first air environment, and (b) repositioning the sorbent to expose the first portion of the sorbent to a second air environment to release the absorbed greenhouse gas therein while the second portion of the sorbent is isolated from the second air environment. In some embodiments, the method further comprises repeating steps (a) and (b) to alternate between absorbing and releasing the greenhouse gas. In some embodiments, the step of (a) exposing the first portion of the sorbent to the first air environment is done simultaneously with exposing the second portion of the sorbent to the second air environment to release the greenhouse gas therein. In some embodiments, the step of (b) repositioning the sorbent to expose the first portion of the sorbent to the second air environment is done simultaneously with exposing the second portion of the sorbent to the first air environment to absorb the greenhouse gas therein. In some embodiments, the first air environment has a lesser humidity than the second air environment. In some embodiments, the absolute humidity of the first air environment or first compartment is less than about 1 gram per $m^3$, less than about 2.5 grams/$m^3$, less than about 5 grams/$m^3$, less than about 10 grams/$m^3$, less than about 15 grams/$m^3$, or less than about 20 grams/$m^3$. In some embodiments, the sorbent is configured to absorb the greenhouse gas in a low humidity environment and release the greenhouse gas in a high humidity environment. In some embodiments, the absolute humidity of the second air environment or second compartment is greater than about 25 g/$m^3$, greater than about 20 grams/$m^3$, greater than about 15 grams/$m^3$, greater than about 10 grams/$m^3$, or greater than about 5 grams/$m^3$. In some embodiments, the greenhouse gas comprises carbon dioxide. In some embodiments, the first air environment is within a first compartment of a housing open to ambient air. In some embodiments, the second air environment is within a second compartment of a housing open to interior air of a greenhouse. In some embodiments, the step of (b) repositioning the sorbent comprises rotating the sorbent within a housing comprising the first and second air environments. In some embodiments, the sorbent is housed within a spinning element within the housing. In some embodiments, the spinning element comprises a spinning wheel.

FIG. 1 depicts a system 100 for purifying water, in accordance with an embodiment. The depicted enclosure comprises *Lemna* 110, and is positioned across a runoff canal 120 (defined by a field 130) from which contaminated water 140 enters the enclosure. Optionally, a pump 170 may be included to draw contaminated water 140 into the enclosure. Cleaner water 150 exits the enclosure and proceeds downstream. In some embodiments, the enclosure is supplied with a sorbent 180 that is operably configured to alternate between fluid communication with the air within the enclosure and the air outside the enclosure to thereby capture $CO_2$ from the exterior air and release $CO_2$ to the interior of the enclosure in accordance with the various aspects of the invention described herein. In some embodiments, the enclosure is supplied with one or more solar panels 160a, pinwheel wind generators 160b, or LED lights 160c. The solar panels 160a or pinwheel wind generators 160b may be configured to supply power to optional elements that may be included in an embodiment, including a pump 170, a rotating mechanism for sorbent 180, and/or the LED lights 160c.

Figure 2:
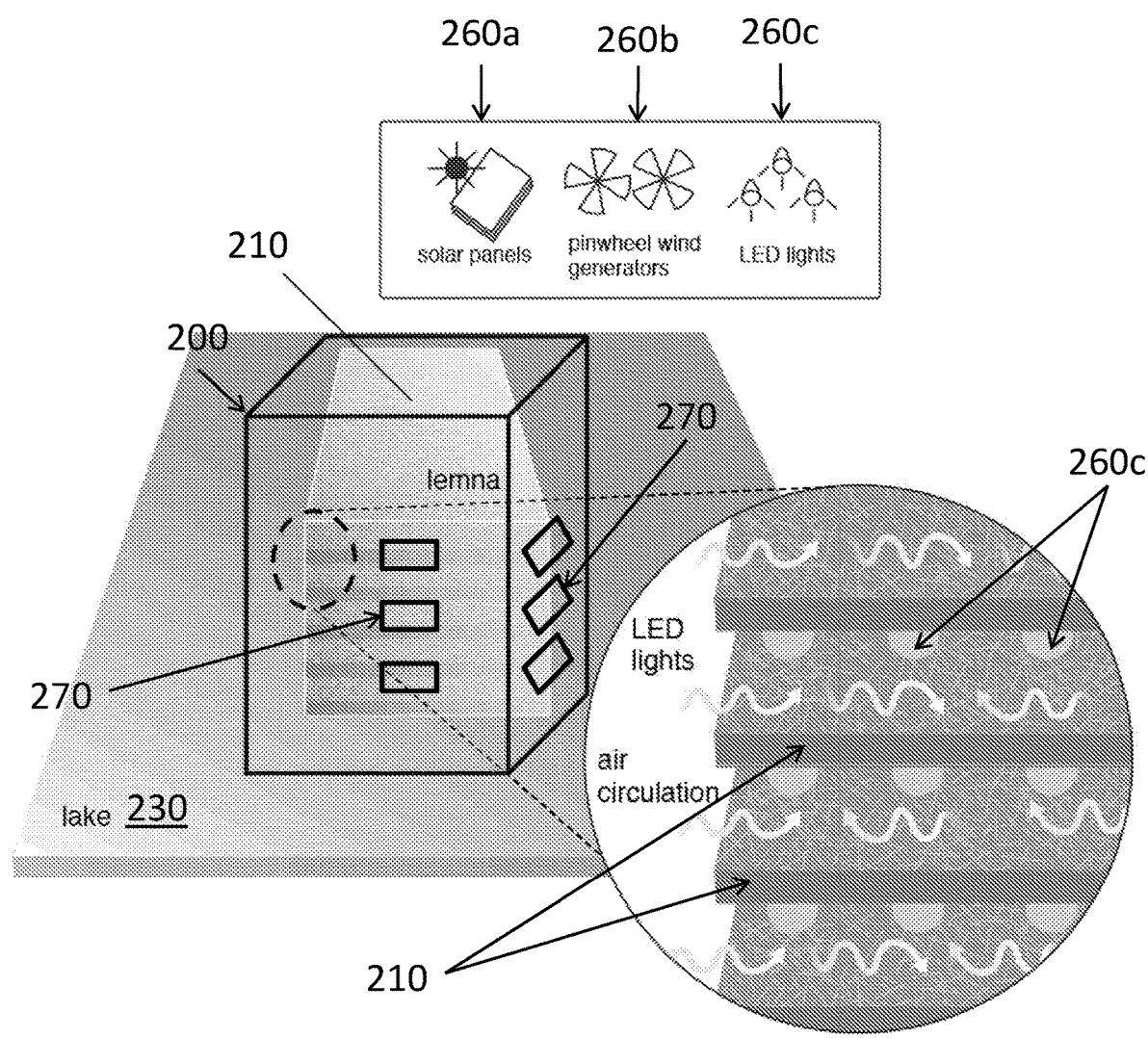
FIG. 2 shows a schematic of a system for purifying water, in accordance with an embodiment.

FIG. 2 depicts a system 200 for purifying water, in accordance with an embodiment. The interior of system 200 may also be included in an enclosure similar to that shown in FIG. 1, including the various optional elements depicted in FIG. 1. The depicted system 200 shown in FIG. 2 comprises multiple vertical layers, each containing *Lemna* 210. The layers are supplied with LED lights 260c. The enclosure housing the *Lemna* 210 is depicted in contact with and surrounded by a lake 230. Contaminated water enters the enclosure, and cleaner water exits the enclosure (through the same or different openings 270). In some embodiments, the enclosure is also supplied with $CO_2$ from a $CO_2$ capture material, which may be configured similar to sorbent 180 shown in FIG. 1. In some embodiments, the enclosure is supplied with one or more solar panels 260a or pinwheel wind generators 260b, and these elements may be configured as shown in FIG. 1.

Figure 3:
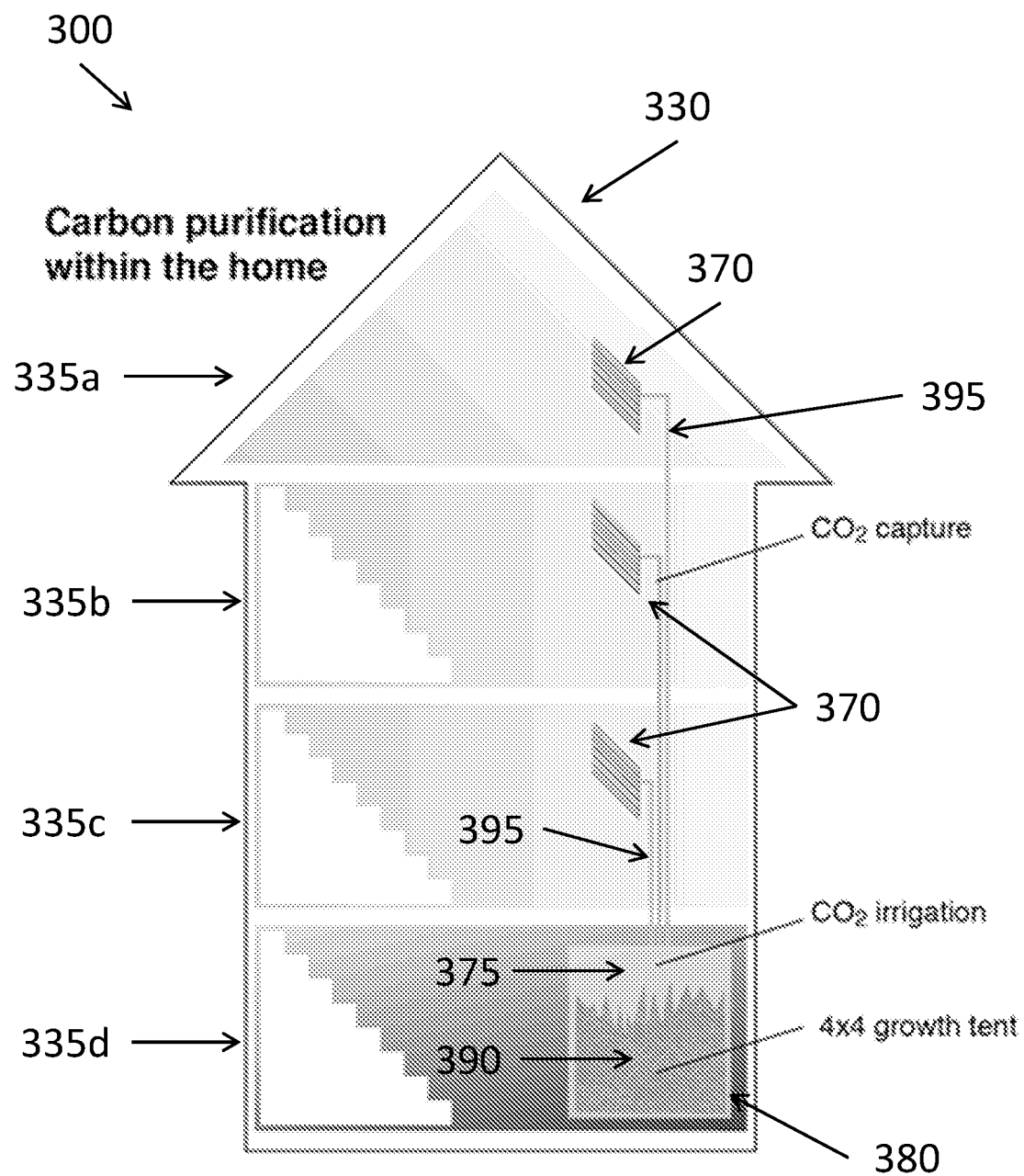
FIG. 3 shows a schematic of a system for enhancing plant growth in a building comprising multiple compartments, in accordance with an embodiment.

FIG. 3 depicts a system 300 for enhancing plant growth in a building 330 comprising multiple compartments (upper or roof compartment 335a, second floor compartment 335b, first floor compartment 335c, and lowest or basement compartment 335d), in accordance with an embodiment. $CO_2$ in air of the upper compartments 335a, 335b, 335c is captured by sorbents 370 and is transferred through conduits 395 and is released to the airspace 375 of an enclosure 380 comprising plants 390 within the lowest compartment 335d. Although the plant compartment is shown as the lowest compartment in FIG. 3, in some embodiments, the plant enclosure may be located within any of the other compartments, and a pump may be used to transfer $CO_2$ from the location of the sorbent to the plant enclosure via $CO_2$ transfer conduits 395.

Figure 4:
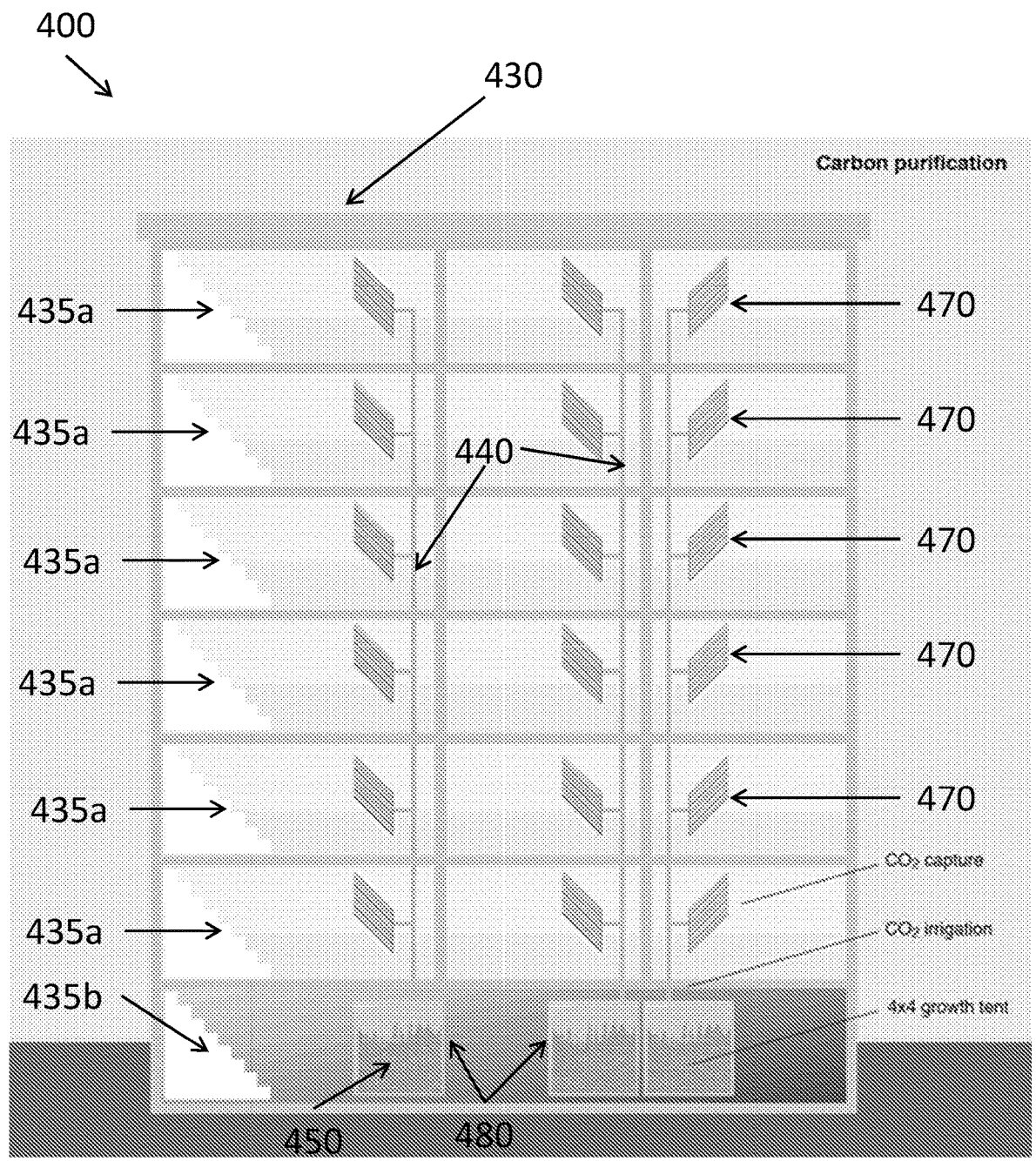
FIG. 4 shows a schematic of a system for enhancing plant growth in a building comprising multiple compartments, in accordance with an embodiment.

FIG. 4 depicts a system 400 for enhancing plant growth in a building 430 comprising multiple compartments (upper compartments 435a and lowest compartment 435b), in accordance with an embodiment. $CO_2$ in air of the upper compartments 435a is captured by sorbents 470 and transferred through conduits 440 and released to enclosures 480 comprising plants 450 within the lowest compartment 435b.

FIGS. 5A-5D depict a greenhouse gas capture and release device or apparatus 500. The capture apparatus 500 is divided into a first compartment 500a and a second compartment 500b by a barrier 510. The capture apparatus 500 is open to both an ambient, atmospheric air environment AA and an enclosed air environment such as greenhouse air GA in a greenhouse GH. In many embodiments, the capture apparatus 500 is used to capture carbon dioxide in ambient air and release the captured carbon dioxide into a greenhouse such that plant life or *Lemna* therein can convert the carbon dioxide into oxygen.

The capture apparatus 500 comprises an air inlet 503a and an air outlet 506a for ambient air AA at the first compartment 500a. The capture apparatus 500 comprises an air inlet 503b and an air outlet 506b for greenhouse air GA at the second compartment 500b.

Figure 5A:
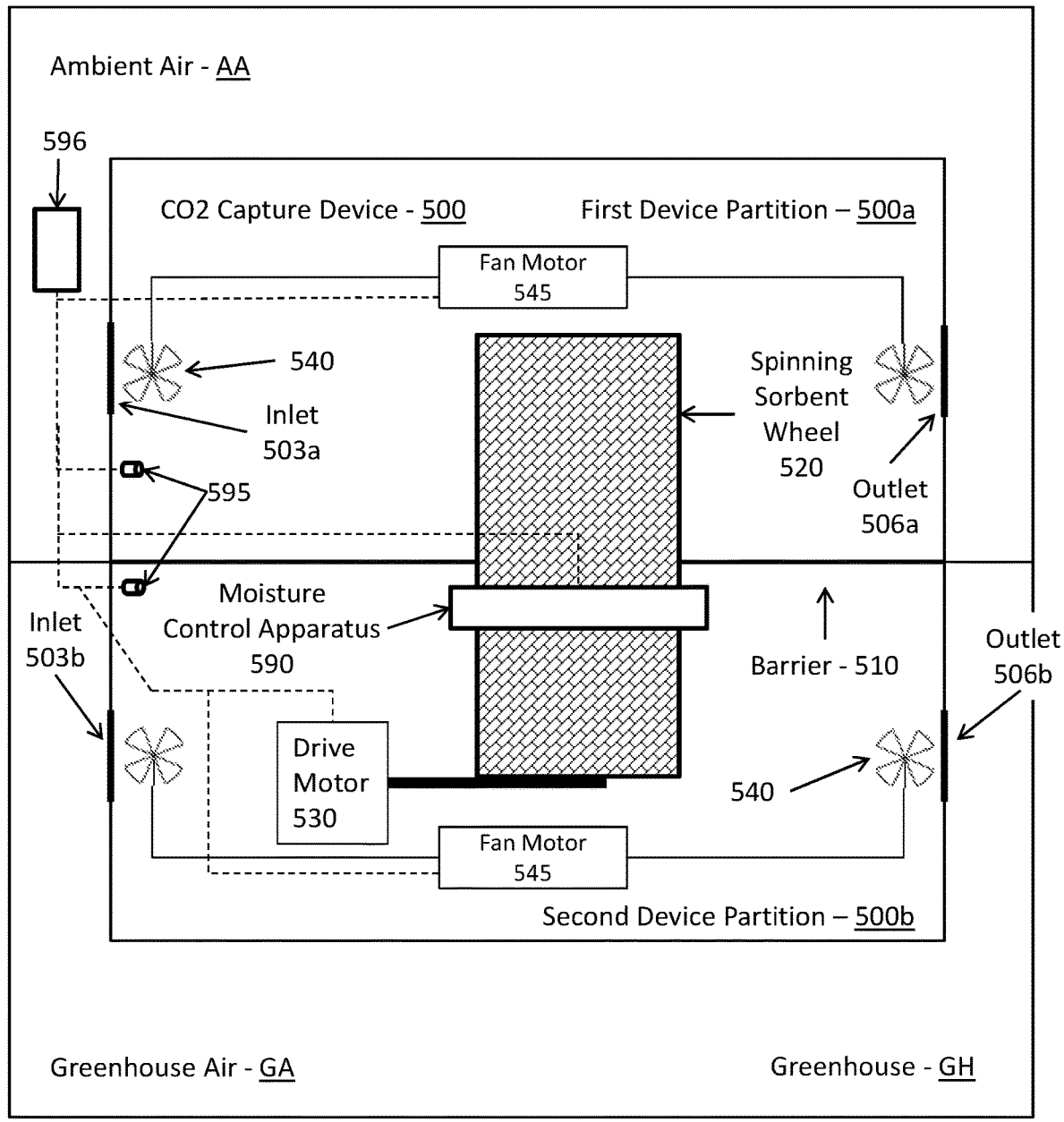
FIG. 5A shows a schematic of an apparatus for capturing and releasing a greenhouse gas, in accordance with an embodiment.
Figure 5B:
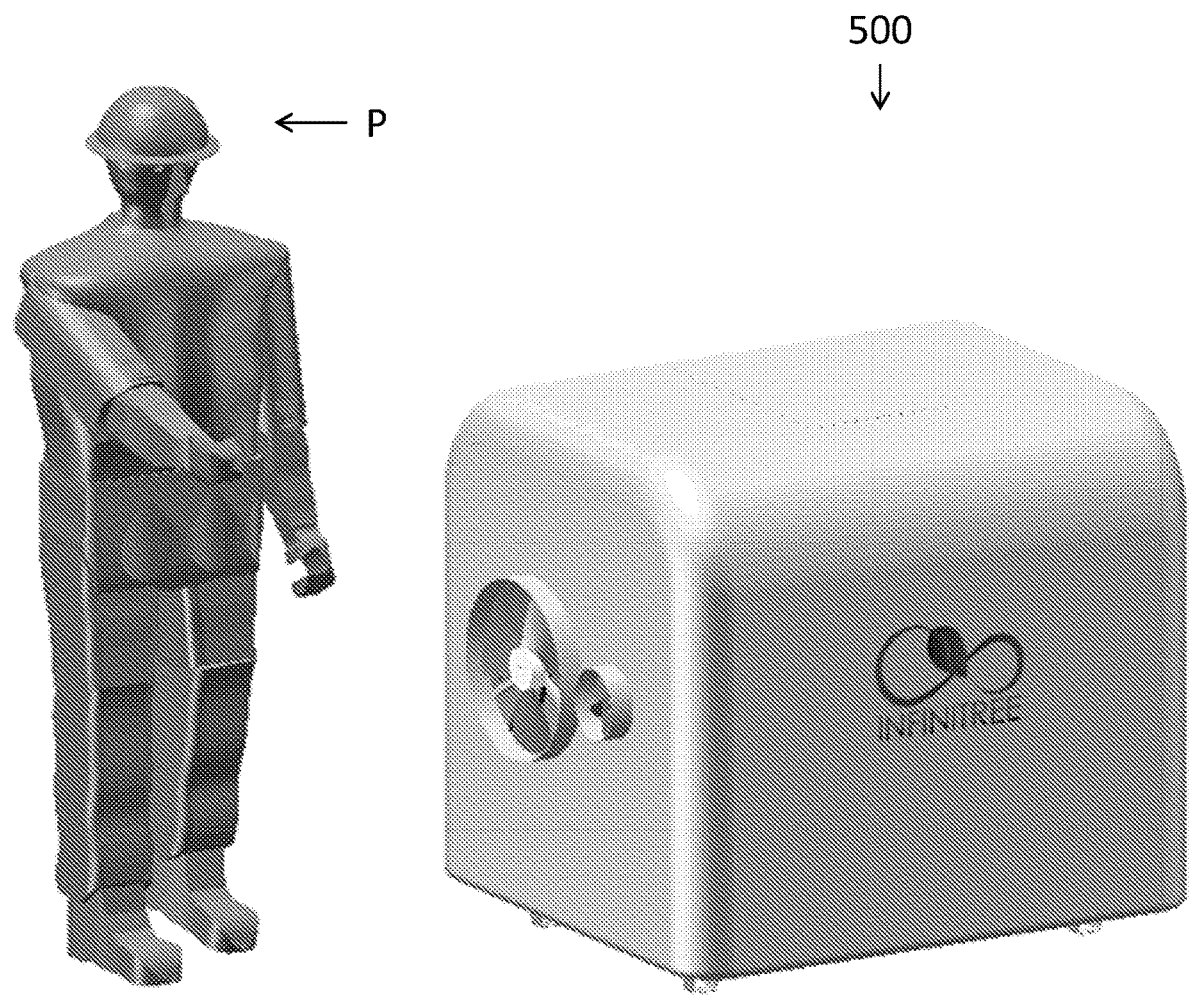
FIG. 5B shows a perspective view of the apparatus of FIG. 5A next to a human being to indicate an exemplary size and shape for the apparatus, in accordance with an embodiment.

In many embodiments, one or more of the inlets or outlets comprise one or more fans 540 to facilitate circulation of air through the first and second compartments 500a, 500b. The fan(s) 540 are actuated by a fan motor 545. As shown in FIG. 5A, for example, the fan motor 545 may be linked to and actuate multiple fans 540.

Figure 5C:
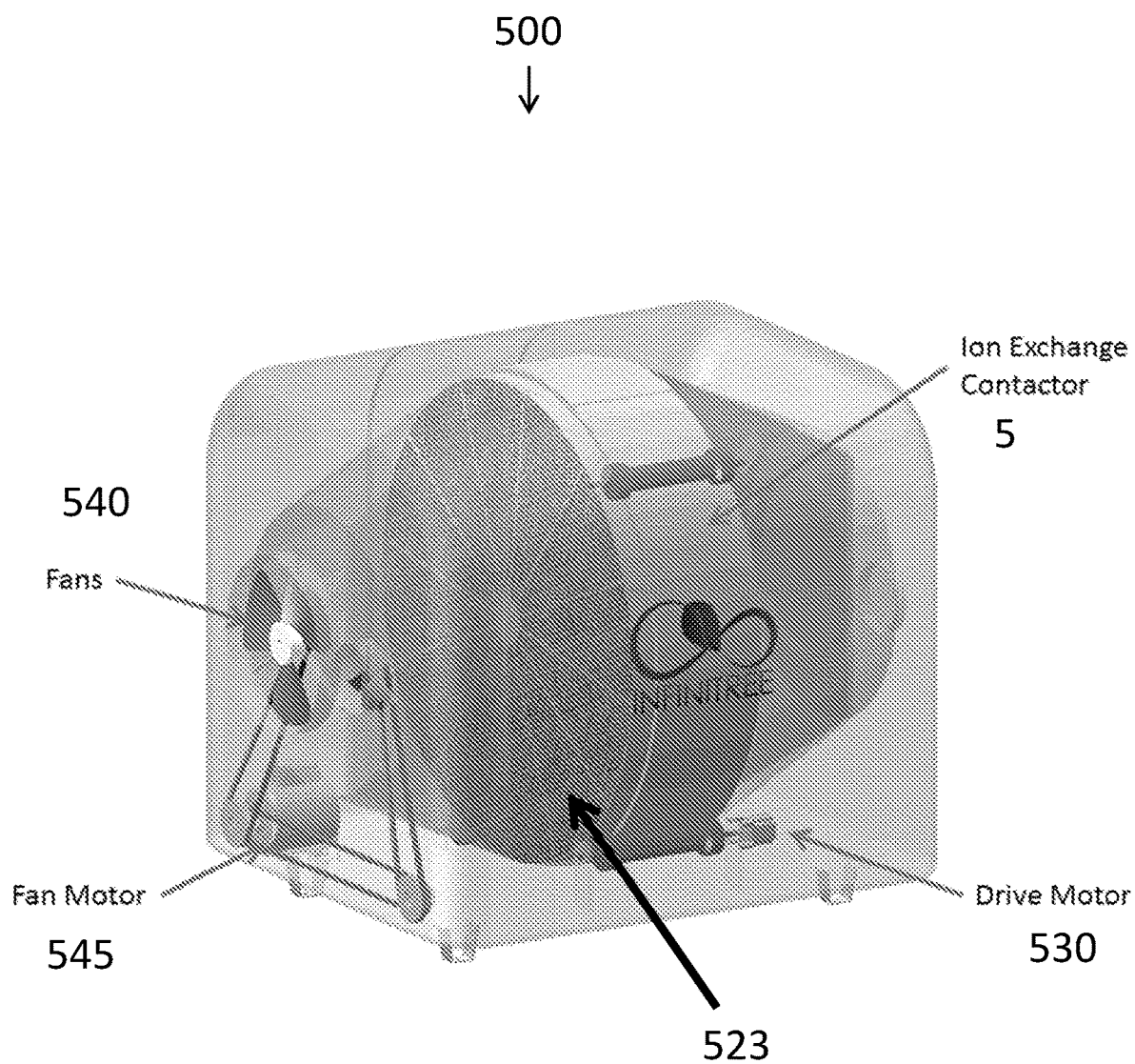
FIG. 5C shows a perspective view of the components of the apparatus of FIG. 5A, in accordance with an embodiment.
Figure 5D:
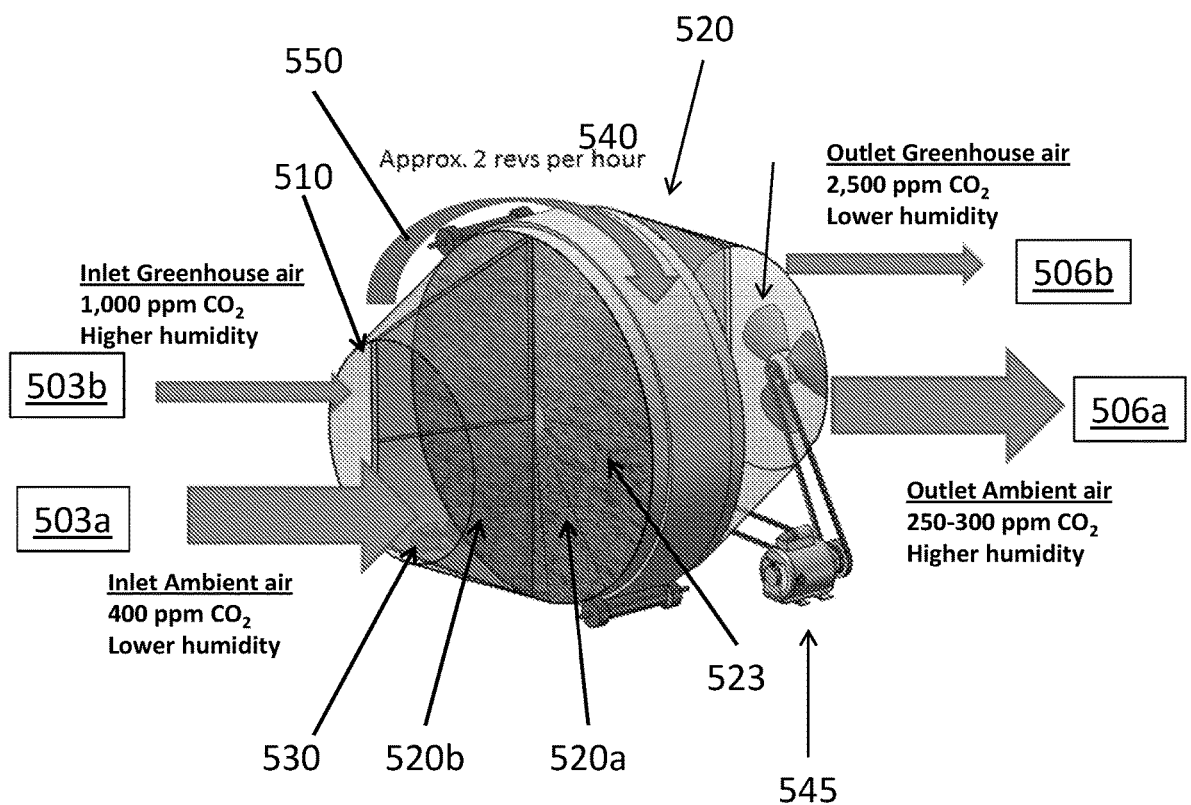
FIG. 5D shows a schematic of the greenhouse gas sorbent element of the apparatus of FIG. 5A, in accordance with an embodiment.
Figure 6:
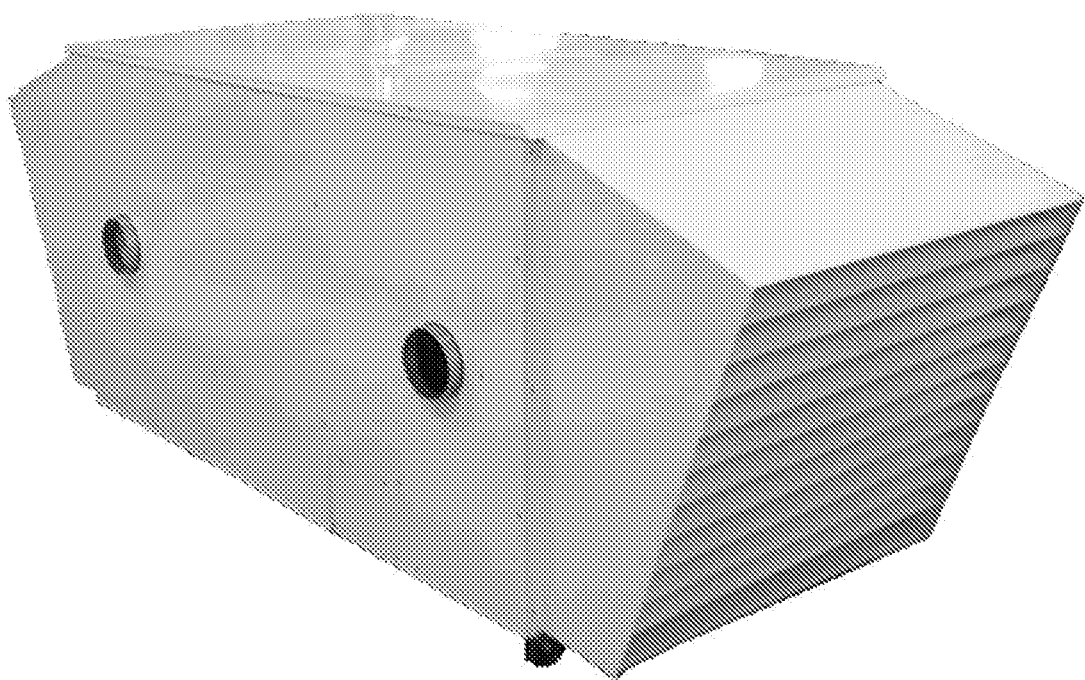
FIG. 6 shows the exterior of a device in accordance with an embodiment, comprising a side having an inlet and an outlet for passage of air from an enclosure (e.g. a greenhouse) into the device, and from the device back into the enclosure, respectively, wherein the device is configured to be located adjacent to the enclosure and connected via the inlets and outlets.
Figure 7:
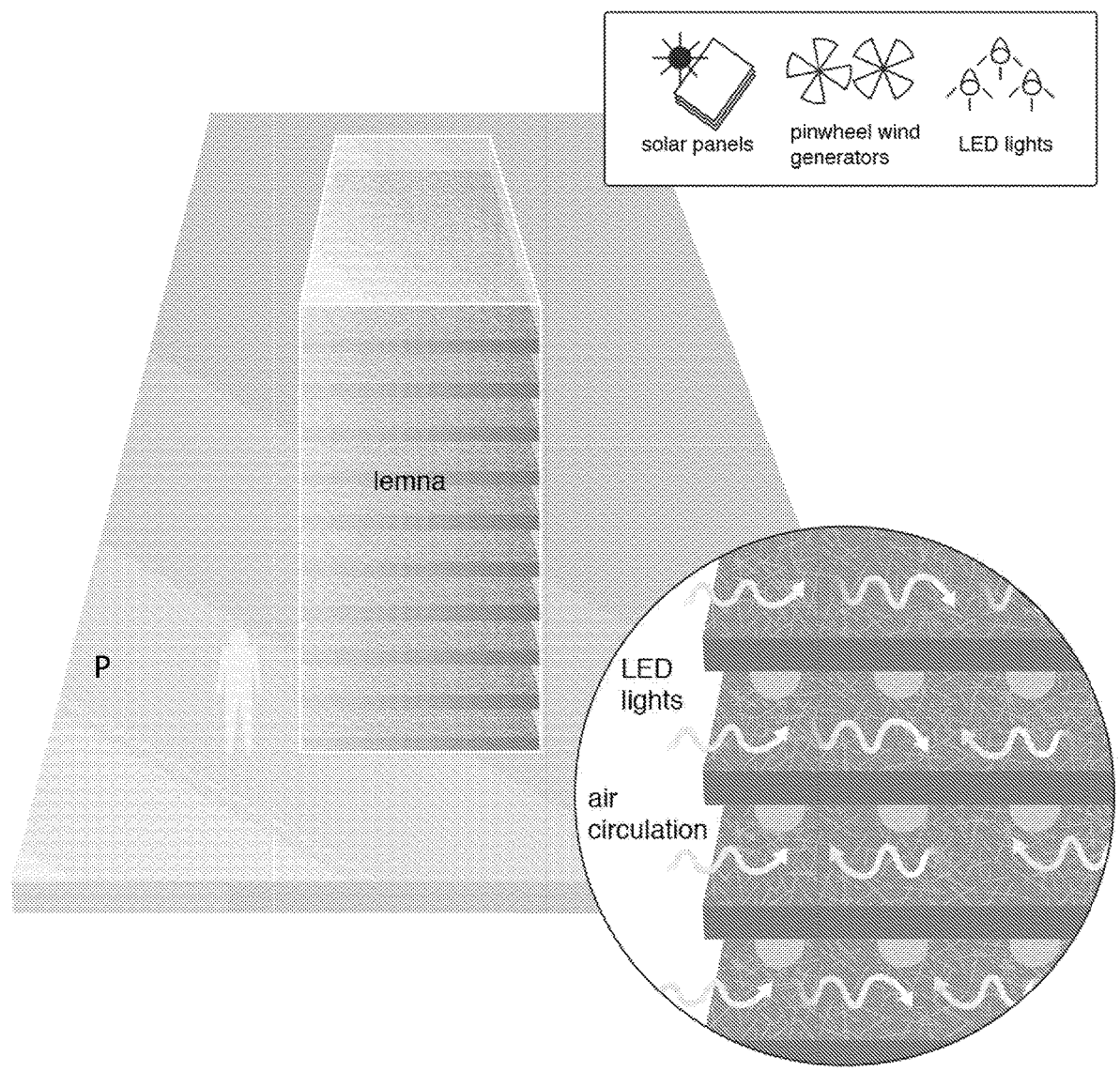
FIG. 7 shows a schematic of a greenhouse in accordance with some embodiments, the greenhouse having multiple stacked tiers comprising growing *Lemna*. The greenhouse is optionally supplied with LED lights, solar panels, and pinwheel generators. A human figure (P) is depicted adjacent to the greenhouse as an example depiction of scale.

The capture device 500 comprises a greenhouse gas exchange material or sorbent 520. When dry or in an environment of relatively low humidity (such as when sitting in first device partition 500a), the sorbent 520 absorbs $CO_2$. When wetted or exposed to an environment of relatively higher humidity in second device partition 500b (such as when exposed to high humidity or directly wetted, such as by spraying, immersion, or dousing with water via moisture control apparatus 590), the sorbent 520 releases $CO_2$. Preferably, the sorbent is a solid sorbent. Examples of solid sorbents for the capture of $CO_2$ from air include, but are not limited to, anion exchange materials, zeolite, activated carbon, activated alumina, solid amines, and other materials capable of physical or chemical adsorption of $CO_2$ molecules. In preferred embodiments, the sorbent comprises an anion exchange material. In some embodiments, the sorbent comprises a support functionalized with an amine, such as a tertiary or quaternary amine. In some embodiments, the sorbent comprises Type 1 or Type 2 functionality anion exchange materials. Non-limiting examples of sorbents for absorbing $CO_2$ are described in U.S. Pat. Nos. 8,999,279 and 8,262,774, the example sorbents of which are incorporated herein by reference. The sorbent 520 in the apparatus 500 is replaceable. In many embodiments, the greenhouse gas sorbent 520 is in the form of a spinning wheel. As shown in FIGS. 5C and 5D, the spinning wheel is divided into a plurality of (pie) slice-shaped segments 523 which are isolated from one another. In some embodiments, the wheel comprises a spiral-wound sheet of sorbent material, which may be maintained in a wound configuration by placing the wound wheel within a rigid structure (e.g. a ring) that prevents unwinding. In one example, the sorbent is formed by rolling a single-face corrugated structure, in which the corrugations are aligned axially, creating parallel air channels. In some embodiments, the wheel has a diameter from about 1 foot to 2 meters, or more. In some embodiments, the wheel has a thickness of about 1 meter or less. Corrugation height may be about 0.25 inches or larger.

The capture device 500 circulates air through the sorbent 520, and the sorbent 520 absorbs the greenhouse gas. As shown in FIG. 5D, ambient air AA is circulated from the inlet 503a, through the sorbent 520, and out through the outlet 506a. The sorbent 520 absorbs carbon dioxide from the circulated air. For example, ambient air going toward the sorbent may comprise less than 800 ppm (e.g. about 400 ppm) $CO_2$ while air going out away from the sorbent back to the ambient environment may comprise a reduced amount of $CO_2$ (e.g. about 250-300 ppm $CO_2$ or less). Furthermore, the sorbent 520 is configured to absorb $CO_2$ in a relatively low humidity environment and release $CO_2$ in a relatively high humidity environment. In some embodiments, the first compartment 500*a* is divided into a low humidity portion at the inlet 503*a* and a high humidity portion at the outlet 506*a*, such as by the sorbent 520 itself, as shown in FIG. 5D. Likewise, the second compartment may be divided into a relatively high humidity portion and a relatively low humidity portion. In some embodiments, the humidity differences on either side of the sorbent are a consequence of humidity changes associated with capture and release of $CO_2$. For example, $CO_2$-laden sorbent may be exposed to higher humidity in the second compartment, with some water being absorbed by the sorbent as $CO_2$ is released from the sorbent, such that air exiting the second compartment is relatively reduced in humidity. As the absorbed water enters the first compartment, water is released as the relatively drier air of the first compartment passes through the sorbent, which releases water in the form of increased humidity while absorbing $CO_2$. Changes in humidity across the sorbent are relative between entering and exiting air. The relatively "low humidity" exiting the second compartment (as compared to humidity entering the second compartment) may in some cases be of a higher humidity than the "high humidity" exiting the first compartment.

Similarly, greenhouse air GA is circulated from the inlet 503*b*, through the sorbent 520, and out through the outlet 506*b* as shown in FIG. 5D. The sorbent 520 absorbs carbon dioxide from the circulated air. For example, greenhouse air going toward the sorbent may comprise about 1,000 ppm $CO_2$ while air going out away from the sorbent back to the greenhouse environment may comprise a greater level of $CO_2$ (e.g. about 2,500 ppm or more $CO_2$). In some embodiments, the second compartment 500*b* is divided into a high humidity portion at the inlet 503*b* and a low humidity portion at the outlet 506*b*, such as by the sorbent 520 itself. As noted above, changes in humidity across the sorbent are relative between entering and exiting air.

As shown in FIG. 5D, the sorbent 520*a* comprises a first portion 520*a* exposed to ambient air and a second portion 520*b* exposed to greenhouse air. These portions progressively alternate with one another between exposure to ambient and greenhouse air as the sorbent 520 is rotated by motor 530 in a direction shown by arrow 550. In some embodiments, the sorbent 520 fully rotates twice per hour. In this manner, carbon dioxide absorbed on the low humidity, ambient air side by the sorbent 520 is released on the high humidity, greenhouse air side. In some embodiments, the greenhouse air side, the ambient air side, or both the greenhouse and the ambient air sides may comprise one or more sensors 595 configured for detecting humidity, temperature, and/or $CO_2$ level (shown in FIG. 5A). In some embodiments, one or more of (1) the rotation speed of the sorbent (i.e., drive motor 530), (2) the fan 540 speed (i.e., fan motor 545) on the greenhouse air side, (3) the fan 540 speed on the ambient air side, and/or (4) the moisture provided by the moisture control apparatus 590, is adjustable through a controller 596 which may comprise and/or communicate a processor, so as to achieve a desired rate of $CO_2$ capture and/or desired level of $CO_2$ in the greenhouse. In some embodiments, rotation speed is regulated in response to one or more sensors 595 having a $CO_2$ level setpoint on controller 596, such that rotation speed is modulated if the level of $CO_2$ in the greenhouse deviates from the setpoint. Standard known carbon dioxide sensors and humidity sensors may be used, and basic programming can be incorporated into a controller 596 to achieve the desired monitoring/controlling as described herein. The rotary system easily allows the system to self-adjust by rotating faster or slower depending on the $CO_2$ demanded by the growing duckweed and the rate of $CO_2$ adsorption which is dependent on the ambient conditions.

In some embodiments, one or more sensors may be configured to detect the level of $CO_2$ on the ambient air and/or greenhouse side of the system. In further configurations, the system may comprise a control mechanism or control system configured to adapt the rotation of the sorbent based on feedback or calculations made using information derived from one or more sensors (e.g. humidity, temperature, $CO_2$ concentration, etc.) placed on the ambient air and/or greenhouse sides of the system. In some embodiments, the control mechanism or control system may be further integrated into mechanisms regulating the ambient air and/or greenhouse conditions. Mechanisms on the ambient air side of the system that may be detected and/or fed back into the control system may comprise detectors for the time of day, motion sensing, occupancy sensing, humidity, or any other sensors and/or detectors that provide feedback regarding the number of mammals or the rate of $CO_2$ production estimated to occur in the one or more ambient chambers. Mechanisms on the greenhouse side of the system that may be detected and/or fed back into the control mechanism or control system may include temperature, light, water, nutrient, and/or other characteristics of the greenhouse that may induce or otherwise impact the rate of $CO_2$ production by biomass grown in the greenhouse.

In many embodiments, the sorbent 520 removes 100-150 ppm of $CO_2$ from atmospheric or ambient air and boost $CO_2$ concentration by 1,500-2,000 ppm within the greenhouse environment (or up to 1.5-2.0%). In many embodiments, when more $CO_2$ is needed in the greenhouse, the sorbent 520 is spun faster, and when less $CO_2$ is needed in the greenhouse, the sorbent 520 is spun slower. The device may also be sized to accommodate $CO_2$ capture needs.

In some embodiments, methods and systems of the present disclosure utilize aquatic macrophytes in the purification of water or for biomass production in growth tent. Examples of aquatic macrophytes include, but are not limited to, *Eichhornia*, *Spirodela*, *Salvinia*, *Azolla*, *Lemna*, *Pistia*, heartleaf, and members of the duckweed family. Aquatic macrophytes may grow as a single type, or as combinations of different types (e.g. 2, 3, 4, 5, or more different types). In some embodiments, the macrophyte is *azolla* or a duckweed. In preferred embodiments, the macrophyte is a duckweed. In general, duckweed refers to a small, light green, free-floating plant of the Lemnaceae family. The Lemnaceae family comprises four genera (*Lemna*, *Spirodela*, *Wolffia*, and *Wolffiella*) and at least 37 identified species. Duckweed can be found around the world, where it inhabits fresh or brackish, nutrient-rich. Nutrients from the water are taken up by the plant and assimilated into protein, which can exceed 40% dry weight of the plant. Examples of duckweed include, but are not limited to: genus *Spirodela* (*S. polyrrhiza*, *S. intermedia*, *S. punctata*); genus *Lemna* (*L. aequinoctialis*, *L. disperma*, *L. ecuadoriensis*, *L. gibba*, *L. japonica*, *L. minor*, *L. miniscula*, *L. obscura*, *L. perpusilla*, *L. tenera*, *L. trisulca*, *L. turionifera*, *L. valdiviana*); genus *Wolffia* (*Wa. angusta*, *Wa. arrhiza*, *Wa. australina*, *Wa. borealis*, *Wa. brasiliensis*, *Wa. columbiana*, *Wa. elongata*, *Wa. globosa*, *Wa. micro-*

*scopica, Wa. neglecta*) and genus *Wolfiella* (*Wl. caudata, Wl. denticulata, Wl. gladiata, Wl. hyalina, Wl. lingulata, Wl. repunda, Wl. rotunda*, and *Wl. neotropica*). In some embodiments, the duckweed is of the genus *Lemna*. While reference is made to duckweed throughout the present disclosure, it is contemplated herein that duckweed may be replaced or supplemented with the class of aquatic macrophytes or one or more other specific aquatic macrophytes.

In some embodiments, the duckweed is housed in an enclosure or growth tent. Enclosures can take any of a variety of conformations. In some embodiments, the enclosure is positioned partially or entirely on a surface of the body of water. When the enclosure is in direct contact with the body of water, duckweed contained within the enclosure may be growing on a surface of the body of water. In some embodiments, duckweed in the enclosure is contained within a compartment that contains water from the body of water, and is fluidically connected to the body of water (such as by means of one or more conduits, one or more valves, and/or one or more pumps), but is otherwise separated from the body of water. For example, duckweed in the enclosure may be contained within one or more grow beds or tanks. In some embodiments, a plurality of compartments containing duckweed are arranged in vertical tiers within the enclosure, such as in a stack. In some embodiments, a stack comprises about or at least about 2, 3, 4, 5, 6, 7, 8, 9, 10, or more compartments containing water from the body of water and duckweed. In some embodiments, the base dimensions (e.g. length and width) of the compartments are approximately the same, and are centered along a vertical axis. In some embodiments, the base dimensions of the enclosure are approximately the same as the base dimensions of the compartments containing the duckweed, such that each compartment forms a separate layer of the enclosure. Water and/or air of the compartments containing the duckweed may be fluidically connected, such as by way of openings, vents, conduits, or the like. In some embodiments, the compartments are separated by a headspace of about, or at most about 0.25, 0.5, 0.75, 1, 1.5, 2, 3, or 5 meters. In some embodiments, the depth of water within a compartment is about, or at most about 2, 4, 6, 8, 10, 12, 18, or 24 inches.

In some embodiments, the duckweed has an enhanced growth rate. Duckweed in optimal conditions has an exponential growth rate, doubling the number of fronds in 30 hours and producing 64 grams of biomass per gram starting weight in a week. Duckweed's growth rate far exceeds that of terrestrial crops such as corn (2.3 g/g/week), is unencumbered by secondary products such as lignin, and grows water-efficiently unlike crops like corn and soy. In some embodiments, air in the enclosure (such as in a compartment thereof) has a $CO_2$ concentration that is higher than air exterior to the enclosure. Exposure to higher levels of $CO_2$ may be advantageously employed to increase duckweed rate of growth, as well as the rate of removal of contaminants from the water, relative to rates obtained at $CO_2$ concentrations approximating that of outdoor ambient air. The precise concentration within the enclosure may vary. In some embodiments, the $CO_2$ concentration in air of the enclosure is maintained at a level effective to increase the growth rate of the duckweed, and/or the rate of contaminant removal, such as a rate of about or at least about 2-fold, 3-fold, 4-fold, 5-fold, 6-fold, 7-fold, 8-fold, 9-fold, 10-fold, 15-fold, or more as compared to growth in outdoor atmospheric air. In some preferred embodiments, the growth rate is increased at least about 5-fold, such as between 8-fold to 10-fold, or more. Increases in growth rate may be determined by any suitable method, such as measuring biomass increase in a population of duckweed over a specified period of time (e.g. 6 hours, 12 hours, 24 hours, 48 hours, 72 hours, or a week). In some embodiments, the air exterior to the enclosure has a $CO_2$ concentration of less than 800 ppm (e.g. less than 700 ppm, 600 ppm, 500 ppm, or 400 ppm). In some embodiments, air in the enclosure has a $CO_2$ concentration of at least 1000 ppm, 1200 ppm, 1500 ppm, 2000 ppm, 3000 ppm, or higher. In some embodiments, air in the enclosure has a $CO_2$ concentration between 1000 ppm and 3000 ppm, such as between about 1000-about 2000 ppm, about 1000-about 1500 or about 1200-about 1500 ppm.

In some embodiments, the concentration of $CO_2$ in the enclosure is increased by capturing $CO_2$ from air outside the enclosure and delivering the captured $CO_2$ into the enclosure. Preferably, the air from which $CO_2$ is captured is outdoor atmospheric air. Systems and methods of the disclosure may employ any of a variety of sorbents for capturing $CO_2$ from air. Sorbents may be liquid sorbents or solid sorbents. In some embodiments, solid sorbents are preferred, such as a solid sorbent comprising an amine. Examples of solid sorbents for the capture of $CO_2$ from air include, but are not limited to, anion exchange materials, zeolite, activated carbon, activated alumina, solid amines including weak base amines and strong base amines, and other materials capable of physical or chemical adsorption of $CO_2$ molecules. Sorbent may be regenerated through various means, for example through contact with water, humid air, pulses of steam, water vapor, water mist, contact with a secondary sorbent, application of heat (e.g. using a thermal swing or vacuum pressure). Accordingly, systems of the enclosure may comprise a regeneration unit for regenerating the sorbent by subjecting the sorbet to suitable regeneration conditions (e.g. by wetting the sorbent, exposing the sorbent to increased humidity, heating the sorbent, etc.). In many embodiments, the sorbent material for capturing $CO_2$ from air has a $CO_2$-holding ability that depends on humidity. For example, the sorbent may adsorb more $CO_2$ as humidity is decreased (such as when the sorbent dries), and release captured $CO_2$ upon exposure to an increased humidity or wetting with liquid water. Releasing captured $CO_2$ by exposure to increased humidity or wetting is also referred to as a humidity swing. In some embodiments, a sorbent is subjected to a humidity swing by first exposing the sorbent to relatively dry air, followed by exposure to air of higher humidity or directly wetting with water or other ion containing solutions. In arid climates, for example, the sorbent may first be exposed to hot dry air outside an enclosure, where the sorbent can extract $CO_2$ from the open air, and then moved into the warm, humid environment of a greenhouse, where the sorbent is regenerated and $CO_2$ is released. Humidity swing and release of $CO_2$ may also occur when sorbent is exposed to water mists, or other forms of wetting including direct exposure to a body of water, such as by submersion. Once exposed to the increased humidity or liquid water, the sorbent releases the $CO_2$ into the atmosphere or directly into the water. In some embodiments, where the duckweed is contained in a plurality of compartments, $CO_2$ may be delivered to each compartment from a separate sorbent, such that each tier is supplied with a separate solid sorbent.

In some embodiments, the sorbent also captures other gases commonly found in ambient outdoor air, including $SO_x$, $NO_x$, hydrogen sulfide, and ozone. These species do not release from the absorber through the humidity swing process, and the $CO_2$ product stream from the humidity swing process is not contaminated by these species. These species slowly build up within the sorbent over time and reduce the overall capacity of the sorbent. In some embodiments, a secondary regeneration process is performed periodically to remove these species. The secondary regeneration process may comprise washing the sorbent in a low concentration caustic solution. A suitable solution is common baking soda in water. When the sorbent comprises an amine, the caustic solution will effectively cleanse the amine of contaminating gases, and return the amines to 100% effectiveness as sources for $CO_2$ capture. In some embodiments, a method is provided wherein a sorbent is used to capture $CO_2$ from ambient air in accordance with other aspects as described herein, and that sorbent is periodically regenerated by a primary regeneration process comprising exposing the sorbent to $H_2O$ in order to release $CO_2$ therefrom, and is periodically regenerated by a secondary regeneration process comprising exposing the sorbent to a caustic solution to remove other contaminants therefrom. In accordance with this aspect of the invention, the primary regeneration process is done more frequently than the secondary regeneration process.

In some embodiments, the solid sorbent comprises a sorbent material distributed on or in a support material, or formed from a mixture of sorbent material and support material. The support material may be an inert material. Examples of support material include, but are not limited to woven or non-woven fiber matrix of polypropylene polymer, poly (vinyl chloride), polyester, other polymers such as those listed below, and cellulose. The solid support may comprise one or more polymers including polybisphenol-A-carbonate, poly(ethylene terephthalate), polystyrene, poly (methyl methacrylate), poly(vinyl acetate), poly(vinyl chloride), polytetrafluoroethylene, polysulfone, poly(vinylidene fluoride), styrene/butyl acrylate/methacrylic acid terpolymer, and poly(vinylidene fluoride-co-hexafluoropropylene). Additional materials and processes for forming such materials are provided in U.S. Pat. No. 8,262,774, which is incorporated herein by reference. A solid sorbent may take various forms. For example, a solid sorbent may comprise: (1) sheets of solid sorbent material, (2) liquid sorbent coated or painted onto a solid support, (3) sorbent cross-linked into a solid polymer matrix, or (4) sorbent held within one or more frames. A solid sorbent or a solid support that sorbent is painted or coated onto may not be entirely smooth; it may, for example, be roughened by regular or random methods. Roughening may include sand blasting, grinding, or other mechanical means, or etching including chemical or high energy etching, e.g., by bombardment. The surface of the solid sorbent or solid support may be bumpy, including various grooves, dimples, fibrous and abrasive areas, or other dendrites or other small structures. The shapes formed from or otherwise comprising the sorbent may be flexible, or resiliently deformable. The shapes, strips, or pieces of solid sorbent may be arranged within alternate structures—for example strips or threads that may be wrapped, treaded, wound or otherwise dispose from, within, or around a support. The solid $CO_2$ sorbent may be configured to have a high surface area. The solid sorbent or solid support may have: lines for directing air flow, it may comprise corrugated surfaces, a plurality of tubes, angular shapes, and/or honeycomb shapes. The solid sorbent may be a monolithic structure, such as a honeycomb, it may comprise lattices with woven or non-woven material coated with $CO_2$ absorbing materials, or $CO_2$ holding materials, it may further be a combination of monolithic and latticed structures. The sorbent may be formed into shapes (i.e. strips, rods, disks with raised edges, etc.), these shapes may be formed by any number of methods including extrusion, spinning, cutting or slit from a preformed sheet. In some embodiments, the sorbent is formed in a substantially circular shape, such as a disc formed in a spiral pattern to take advantage of a continuous strip of sorbent material. The sorbent sheet may be wound until the desired diameter is achieved. An alternative to this configuration would be discrete increasingly larger diameter annular segments of corrugated solid sorbent and planar sheet subassemblies that would fit snugly together until the desired diameter is achieved. Additional examples of possible configurations are described in U.S. Pat. No. 7,993,432, which is incorporated herein by reference.

In some embodiments, the solid sorbent is distributed about an axis around which the sorbent rotates, such as in a wheel. A portion of the wheel is located outside the enclosure, and captures $CO_2$ from air exterior to the enclosure. A portion of the wheel is located within the interior of the enclosure, and releases $CO_2$ to the enclosure. Rotation about the axis causes a portion of the wheel located outside the enclosure to enter the enclosure, and a portion of the wheel located within the interior of the enclosure to exit the enclosure. The degree of $CO_2$ loading and unloading to and from the sorbent can be modulated by changing one or more parameters, such as the surface area of the sorbent, the diameter of the wheel, the rotation speed, and the fraction of the sorbent inside the enclosure.

In some embodiments, the system, enclosure, or each duckweed-containing compartment within an enclosure comprises additional elements to facilitate growth of the duckweed and operation of the system. For example, the enclosure can comprise an artificial light source, such as for aiding photosynthesis of the duckweed. Examples of artificial light sources include any single or combination of incandescent light sources, gas discharge light sources, light emitting diodes, fluorescent lamps, and High Efficiency Plasma (HEP) lamps. Incandescent light sources include incandescent bulbs, halogen lamps, Nernst lamps, and parabolic aluminized reflector lamps. Gaseous discharge light sources may include fluorescent, high-intensity discharge lights (HID), and low-pressure sodium lights. HID lamps may include lamps that use different gases to produce light, including mercury vapor, metal halide including ceramic metal halide, and high pressure sodium. Light emitting diodes may comprise any single or combination of colors, or range of spectra including full spectrum. Examples of LEDs may include Red LED, Green LED, Blue LED, RGB LED, and white LED. Fluorescent lamps may comprise tube-style fluorescent lights and Compact Fluorescent Lights (CFLs). HEP light sources may comprise any high-efficiency plasma lighting that has system efficiencies of 90 lumens per watt or more. Light sources may be selected to from any range of spectrum, luminous efficacy, and color temperature. In some embodiments, the system comprises a passive power source for powering one or more processes within the enclosure. Non-limiting examples of passive power sources include solar panels, wind turbines, hydroelectric generators (e.g. tidal power, wave power, or hydro-turbines), geothermal energy, and thermal energy converters (e.g. ocean thermal energy).

In one aspect, the present disclosure provides a method of purifying water. In some embodiments, the method comprises: (a) introducing water comprising a contaminant into an enclosure having an interior containing a duckweed, wherein the duckweed removes the contaminant from the water; (b) capturing $CO_2$ from air exterior to the enclosure with a solid sorbent, wherein air exterior to the enclosure has a $CO_2$ concentration of less than 800 ppm; and (c) releasing captured $CO_2$ into the interior of the enclosure, wherein the interior of the enclosure has a higher $CO_2$ concentration than the air exterior to the enclosure. In some embodiments, the method comprises operation of a system as disclosed herein. Water sources, contaminants, duckweeds, enclosures, sorbents, and various parameters of these, including $CO_2$ concentration and other features, may be any described herein, such as with regard to the various systems of the disclosure.

In some embodiments, the method further comprises harvesting duckweed. Harvesting may be performed intermittently, or continuously. The rate or frequency of harvesting may be tuned to allow for a specified degree of duckweed growth. Any of a variety of automated devices for collecting aquatic plants may be advantageously employed. In some embodiments, the automated device is a floating device. In some embodiments, harvesting comprises the operating of a filtration system. Examples of devices for harvesting floating aquatic plants are described in U.S. Pat. Nos. 7,022,223, 5,197,263, US20120117869, and U.S. Pat. No. 5,636,472. In some embodiments, duckweed collected from the water purification system is used in the production of another product. In some embodiments, oil is collected from the duckweed. A variety of processes are available for extracting oil from duckweed, such as pressing and/or boiling the duckweed. Processes for removing oil from duckweed may include mechanical, chemical or combined mechanical and chemical methods. Mechanical methods may include expression/expeller pressing, ultrasonic-assisted extraction, and homogenization. Chemical methods for extracting oil from duckweed may include supercritical fluid extraction, and solvent extraction including hexane solvent extraction and Soxhlet extraction. Oil collected from the duckweed may then be further used as a feedstock in the production of fuel, such as a biodiesel, biobutanol, biogasoline, natural gas including methane, ethanol, green diesel or hydrotreated vegetable oil, and jet fuel. Biodiesel may be made by reacting the oil derived from the duckweed with an alcohol to produce fatty acid esters which may be used alone or blended with petrodiesel. Duckweed biomass may be further used to generate one or more additional fuel sources including biobutanol, biogasoline and ethanol in a biorefinery, which takes various biomass sources and converts them to one or more fuel sources. Alternatively, the biomass could be treated similarly to algae in the Algenol system which uses seawater and industrial exhaust to produce ethanol. Natural gas including methane may be produced from biomass that has undergone one or more methods for producing natural gas from biomass including gasification, pyrolysis and anaerobic digestion. Oil derived from the duckweed may also undergo the hydrotreating refinery process, which breaks down the oil molecules to form green diesel.

In some embodiments, a carbon-neutral fuel is produced by using duckweed collected from the enclosure as a feedstock for ethanol production. The growth of duckweed and/or the ethanol production may be done in a desert. Duckweed cultivation will require 1:3:1 gallons of water per gallon of ethanol produced (e.g. ranging from about 1:1 to about 10:1), and water may be recycled in the cultivation process. In some embodiments, this process will be devoid of fertilizer, pesticide and herbicide, and therefore will not contribute to river and delta dead zones. Carbon fixed by the feedstock will be returned to the atmosphere upon burning resulting in a carbon-neutral fuel. The ethanol feedstock system in accordance with this embodiment would use less energy by comparison with corn ethanol production.

In some embodiments, duckweed collected from the enclosure is used in the production of a food product, a fertilizer and/or starch. Such processes may be secondary to a first procedure, such as oil collection as described above. The food product may be an animal feed. The resulting animal feed may be dry or non-dry. Duckweed biomass may be dried and fed directly, or mixed with other components before feeding. Non-dry animal feed may be wet or moist; it may be made from dried or non-dried duckweed biomass. Duckweed biomass may be fed directly or mixed in with other components for example, fish meal, rice bran, maize meal, soybean meal or other components to produce compound feed. It may be provided as flakes, extruded into pellets, formed into cakes, a powder, a meal, or a mash. Starch that is separated from the other duckweed components may be used to produce a number of commercial products including food, feed, cement, medicine and pharmaceuticals, for paper, glues and other adhesives, ceramics and construction materials (including cement), textiles, cosmetics, colors, printing, chocolates, confectionary, dairy products and desserts, processed foods, deep-frozen foods, sauces and soups, meat and fish products, gelatin and candy, as a basic material for fermentation of chemicals, as sugar alcohol inputs for the chemical industry, plastic, biodegradable plastic packaging, for "clean-label" packaging of foods (without phalates), healthy-choice food products (a starch-based product that neutralizes 66% starch absorption in the body), as a core feedstock for industry chemical and energy industry for fermentation—(much cheaper than sugar), and as recommended by vegetarian and religious organizations worldwide as an alternative to forbidden foods containing gelatin.

In one aspect, the present disclosure provides a system for enhancing plant growth. In some embodiments, the system comprises: (a) a habitable enclosure comprising a plurality of compartments, wherein at least one first compartment comprises a growing photosynthetic biomass and at least one second compartments comprises one or more mammals that exhale $CO_2$ into air of the at least one second compartment; (b) one or more solid sorbents in fluid communication with the at least one second compartment, wherein (i) the one or more solid sorbents is operable configured to capture $CO_2$ in the air of the at least one second compartment, and (ii) the air of the at least one second compartment has a $CO_2$ concentration of 1% or less; and (c) one or more conduits fluidically connecting the one or more solid sorbents and the at least one first compartment through which $CO_2$ released from the one or more solid sorbents is delivered to the at least one first compartment; wherein (i) $CO_2$ in air in the at least one first compartment is maintained at a level that is higher than the $CO_2$ concentration in the at least one second compartment, and (ii) the solid sorbent releases captured $CO_2$ upon wetting or exposure to increased humidity.

Plant growth and crop yield can be improved by increasing the carbon dioxide level in greenhouse air. Conversely, increased levels of carbon dioxide can have negative health impacts on mammals, such as humans. In some embodiments, systems and methods of the disclosure are advantageously employed in removing carbon dioxide from one or more inhabited compartments of an enclosure, and delivering the captured carbon dioxide to another compartment containing a photosynthetic biomass. Enclosures comprising these compartments are typically habitable, and may take any of a variety of forms, such as apartment buildings, office buildings, hotels, houses, warehouses, restaurants, retail buildings, and any other like constructions. Typically, the compartment comprising the photosynthetic biomass is designed as a greenhouse. The term "greenhouse" is used herein to be interchangeable with "compartment comprising a photosynthetic biomass." A greenhouse may comprise one or more components for regulating or monitoring plant growth conditions. Plant growth conditions may include temperature, light, humidity and carbon dioxide. In some embodiments, the greenhouse temperature is maintained below 105° F., 100° F., 95° F., 90° F. or 85° F., or between about 70° F. to about 105° F., about 75° F. to about 100° F., about 75° F. to about 95° F., or about 75° F. to about 85° F. At these temperatures the atmospheric pressure within the greenhouse is at least 10 psi, 11 psi, 12 psi, 13 psi, or 14 psi. Components for regulating or monitoring plant growth conditions may comprise one or more sensors, timers, irrigation systems including hoses and sprayers, or light fixtures. Examples of sensors include temperature sensors, humidity sensors, water sensors including water rope sensors, gas sensors including carbon monoxide or carbon dioxide sensors, dry contact sensors, volt/current meters or sensors, pH probes or sensors, light sensors, pressure sensors, and liquid level sensors. Sensors may trigger alerts, for example remote alerts that notify conditions that meet or exceed a pre-set range. The greenhouse compartment may be connected with the other compartments of the enclosure in any suitable orientation. In one example, the greenhouse may comprise walls that are separate from and located interior with respect to outer walls of the enclosure, such as in a room of a house or the basement of an office building. In another example, one or more walls of the greenhouse form an exterior wall of the enclosure, such as a rooftop greenhouse, or a greenhouse located adjacent to a house and connected by a door or hallway. In some embodiments, the greenhouse is located below one or more of the other compartments, such as is illustrated in FIGS. 3 and 4. In some embodiments, the biomass is in a growth tent.

The greenhouse compartment may comprise a variety of features conducive to plant growth. A greenhouse compartment may comprise integrated systems for sensing and regulating plant growth conditions. Plant growth conditions may include temperature, light, water/humidity and gas concentrations, for example carbon dioxide gas.

The growing photosynthetic biomass within an enclosure of the disclosure can be any one or more of a variety of photosynthesizers. Typically, the photosythesizer is a plant. The term "plant" encompasses all annual and perennial monocotyldedonous or dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*. In some embodiments, the photosynthetic biomass comprises one or more plants of the same or different type. The plant may be edible, such as in a crop plant. Among the crop plants and other plants that may advantageously be employed as photosynthetic biomass are, for example, rice, maize, wheat, millet, rye, oat, barley, sorghum, sunflower, sweet potato, cassava, alfalfa, sugar cane, sugar beet, canola and other *Brassica* species, sunflower, tomato, pepper, soybean, tobacco, melon, lettuce, celery, eggplant, carrot, squash, melon, cucumber and other cucurbits, beans, cabbage and other cruciferous vegetables, potato, tomato, peanut, pea, other vegetables, cotton, clover, cacao, grape, citrus, strawberries and other berries, fruit trees, and nut trees. Turf grass, ornamental species, such as petunia and rose, and woody species, such as pine and poplar, may also be used.

In one aspect, the apparatus and methods described herein are used to increase $CO_2$ concentration for enhancing the growth of crops, e.g. within a greenhouse with enhanced $CO_2$ concentration. Using such apparatus and methods $CO_2$ concentration is increased to 650 ppm or 1200 ppm, and the yield for the following crops is increased by at least the amounts indicated as compared to growth at 350 ppm $CO_2$:

| Crop | 650 ppm | 1200 ppm |
| --- | --- | --- |
| Barley | 66% | 120% |
| Rapeseed | 62% | 110% |
| Rice | 37% | 65% |
| Sunflower | 36% | 65% |
| Wheat | 43% | 75% |
| Legume ave. | 44.3% | 80% |
| Fruit ave. | 24% | 40% |
| Vegetable ave. | 36.5% | 65% |
| Carrot | 60% | 110% |
| Cassava | 87% | 155% |
| Potato | 35% | 60% |
| Sweet potato | 46% | 80% |
| Cucumber | 39% | 70% |
| Eggplant | 54% | 95% |
| Lettuce | 40% | 70% |
| Tomato | 20% | 35% |

Sorbents that capture $CO_2$ from the air within the one or more second compartments are used to regulate $CO_2$ levels and distribution within and among the compartments of the enclosure. The sorbent can be any of the sorbents described herein, such as with respect to systems for the purification of water, including with respect to sorbent materials, conformations, and constructions. To capture $CO_2$ from air of the one or more second compartments, the sorbent is disposed within the compartment from which $CO_2$ is to be captured, or is in fluid contact with one or more mechanisms, including valving between the capture and release. Examples of methods for valving and release may include pipes, vents, ducts (e.g. ducts within a Heating, Ventilation, and Air Condition or HVAC system). Vents or ducts may comprise $CO_2$ sensitive valves, sensors, or intermediate valves for transferring the captured $CO_2$ through multiple compartments, enclosures, floors and/or rooms within an indoor living or working space. The captured $CO_2$ may then be transferred to the growth tent or chamber. In some embodiments the growth tent or chamber may be in the basement of an indoor living or working space with one or more valves, ducts, pipes or mechanisms for connecting the $CO_2$ to the basement.

In some embodiments, the sorbent has a $CO_2$ holding ability that varies with humidity. Accordingly, the system may further comprise one or more stores of water (e.g. one for each of a plurality of sorbents in the system), and/or one or more dispensers that deliver water in liquid or vapor form to the one or more solid sorbents. For example in some embodiments a store of water may be present in each compartment. In other cases a sprinkler systems may be used to disperse stored water to maintain a fixed range of humidity and moisture in each enclosure. In some embodiments a water source or stored water may be coupled to a heating system that evaporates the stored water to retain a set humidity range. In some embodiments, humidity may be established using a swamp cooler or humidifier. In further embodiments a humidifier may comprise a cool humidifier (e.g. ultrasonic humidifier) or a warm humidifier (e.g. vapor humidifier).

In operation, the system is configured to maintain $CO_2$ in the one or more second compartments below a target level, while maintaining $CO_2$ in the greenhouse above a target level. The concentration of $CO_2$ outside the enclosure may differ from the concentration inside the growth tent. In some cases the growth tent may comprise a different concentration of $CO_2$ outside the growth tent than inside the growth tent. In further embodiments, the concentration of $CO_2$ in the enclosure may comprise greater than or equal to 50 ppm, greater than or equal to 100 ppm, greater than or equal to 200 ppm, greater than or equal to 300 ppm, greater than or equal to 400 ppm, greater than or equal to 500 ppm, greater than or equal to 600 ppm, greater than or equal to 700 ppm, greater than or equal to 800 ppm, greater than or equal to 900 ppm, greater than or equal to 1000 ppm, or greater than or equal to 5000 ppm. In further embodiments, the concentration of $CO_2$ in the growth tent, may comprise greater than or equal to 50 ppm, greater than or equal to 100 ppm, greater than or equal to 200 ppm, greater than or equal to 300 ppm, greater than or equal to 400 ppm, greater than or equal to 500 ppm, greater than or equal to 600 ppm, greater than or equal to 700 ppm, greater than or equal to 800 ppm, greater than or equal to 900 ppm, greater than or equal to 1000 ppm, or greater than or equal to 5000 ppm. In further embodiments, the concentration of $CO_2$ inside the growth tent may be "about 405 ppm" or between 300 and 500 ppm, and the concentration of $CO_2$ inside the growth tent may be "about 650 ppm" or between 550 ppm and 750 ppm. In one embodiment the concentration of $CO_2$ inside the growth tent is between about 1500 to about 6000 ppm and duckweed within the growth tent grows at 4-8 times its growth rate in 400 ppm $CO_2$, which is the approximate level of $CO_2$ in atmosphere. The concentration range of $CO_2$ may change depending on the conditions of the enclosure. The system may be configured to maintain $CO_2$ in the one or more second compartments below a target level, while maintaining $CO_2$ in the greenhouse above a target level. The system may comprise a control system with one or more control mechanisms adapted to maintain $CO_2$ levels of least one compartments, within a specific range or above or below a specific set point. In some embodiments a control systems may comprise a system of sensors and/or detectors configured to detect the level of $CO_2$ on the ambient air and/or greenhouse side of the system. Control systems may further comprise an algorithm for predicting and/or responding to feedback from the one or more sensors. In further configurations, the system may comprise a control mechanisms or a control system configured to adapt the rotation of the sorbent, the speed of fans that control air flow through the system, and/or the amount of moisture applied to the sorbent to facilitate release of $CO_2$, based on feedback or calculations made using information derived from one or more sensors (e.g. humidity, temperature, $CO_2$ concentration, etc.) placed on the ambient air and/or greenhouse sides of the system. In some embodiments, the control mechanism or control system may be further integrated into mechanisms regulating the ambient air and/or greenhouse conditions. In some embodiments, the rotation speed of the sorbent may be regulated by the control mechanisms or control system, may be configured to achieve a desired rate of $CO_2$ capture and/or desired level of $CO_2$ in the greenhouse. In some embodiments, rotation speed of the sorbent is regulated by the control mechanisms or control system in response to a sensor having a $CO_2$ level setpoint, such that rotation speed is modulated if the level of $CO_2$ in the greenhouse deviates from the setpoint.

Sensors or detectors on the ambient air side of the system may be detected and/or fed back into the control system. Sensors on the ambient air side of the system may comprise mechanisms for detecting or sensing the time of day, motion of mammals or occupants, quantity of mammals or occupants, humidity in one or more compartments, $CO_2$ in one or more compartments, or any other sensors and/or detectors that provide feedback regarding the number of mammals or the rate of $CO_2$ production estimated to occur in the one or more ambient chambers. Mechanisms on the greenhouse side of the system that may be detected and/or fed back into the control mechanism or control system, and or controlled by the control system or control mechanism, may include temperature, light, water, nutrient levels, humidity levels, $CO_2$ levels, and/or other characteristics of the greenhouse that may induce or otherwise impact the rate of $CO_2$ production by biomass grown in the greenhouse.

Sorbents for capturing $CO_2$ may be installed as a component of other environmental regulation systems. For example, one or more sorbents may be installed downstream of an intake for a forced-air system for regulating temperature in one or more of the at least one second compartments. One or more compartments may be distributed through multiple compartments (e.g. floors and/or rooms) within of an indoor living or working space. The one or more compartments may be in fluid, air, or fluid and air contact with the one or more compartments. $CO_2$ captured on the sorbent may be transferred to the growth tent or chamber. In some embodiments the growth tent or chamber may be in the basement of an indoor living or working space with one or more valves, ducts, pipes or mechanisms for connecting the $CO_2$ to the basement.

In one aspect, the present disclosure provides a method of enhancing growth of a photosynthetic biomass in at least one first compartment of a habitable enclosure. In one embodiment, the method comprises (a) capturing exhaled $CO_2$ in air of at least one second compartment of the enclosure with one or more solid sorbents, wherein $CO_2$ in the at least one second compartment is maintained below 0.5%; and (b) releasing captured $CO_2$ into at least one first compartment comprising photosynthetic biomass, wherein (i) $CO_2$ in the at least one first compartment is at a higher concentration than in the at least one second compartment, and (ii) the solid sorbent releases captured $CO_2$ upon wetting or exposure to increased humidity. In some embodiments, the method comprises operation of a system as disclosed herein. The various compartments and their arrangement, sorbents, photosynthesizers, and various parameters of these, including $CO_2$ concentration and other features, may be any described herein, such as with regard to the various systems of the disclosure.

In another aspect of the invention, there is provided a engineered duckweed with (1) lipids amounting to about 10 to about 20% of the plant, or about 12% to about 18% of the plant, or at least about 12% of the plant, or at least about 15% of the plant; and/or (2) oil content of about 0.1% to about 0.2% dry weight, or about 0.12% to about 0.18% dry weight, or at least about 0.12% dry weight, or at least about 0.15% dry weight.

Currently in the US, on average, 0.5 kg of $CO_2$ is released per kWh of electricity produced. In places where more renewable electricity is used, such as California, the rate is only 0.3 kg of $CO_2$ per kWh. The systems and methods described herein may be used to collect over about 7 kg of $CO_2$ per kg released due to electricity consumed. If you also considering the carbon footprint from manufacturing a system in accordance with the present invention, the ratio is slightly reduced to about 6.5. With reasonable improvements to fan efficiency, the ratio improves to 18:1. As the national grid trends towards California's, the ratio improves to over 30:1. In the future with a mostly renewable grid, the systems and methods in accordance with the present invention will capture 50 to 100 times more $CO_2$ than emitted from their operation.

In another aspect of the invention, the rate of photosynthesis and/or plant productivity is increased by growing *Lemna* in a $CO_2$ enriched environment in accordance with other aspects of the present invention. In another aspect of the invention, the *Lemna* grown in a $CO_2$ enriched environment, in accordance with other aspects of the invention, naturally transfers an increased amount of $CO_2$ into the soil, thus using the Earth's own biological sequestration technology. In addition, the *Lemna* grown in a $CO_2$ enriched environment becomes rich in fixed carbon taken from the atmosphere. The $CO_2$ rich carbon may be pumped into underground voids, such as abandoned mines. Assessment of volumes available below ground in abandoned mines is achieved by use of remotely controlled mobile robots equipped with laser range finders enabling precise mapping of well volumes. Pumping will take place from the surface, utilizing image database information inclusive of topographical maps, geological maps, tunnel maps, GPS data, land use maps, well maps, volume maps, and well boreholes and other access points. Buried deep in the well, *Lemna* will retain its starch and prove a permanent means of carbon sequestration. Relative to subterranean $CO_2$ sequestration in sandstone formations where leakage remains a threat, sequestration bound as starch within *Lemna* offers a safer solution.

In another aspect of the invention, the systems described herein sequesters between about 5 to about 20 tons of $CO_2$ per hectare *Lemna* cultivated per year.

In another aspect of the invention a solid sorbent is configured to capture $CO_2$ in air exterior to an enclosure and release the captured $CO_2$ at a higher concentration than captured, and such $CO_2$ is released to the interior of the enclosure. $H_2O$ (in any form, e.g. liquid, vapor, or gas) within the enclosure, or otherwise in communication with the sorbent, induces release of $CO_2$ from the sorbent into the enclosure, and the energy to release the $CO_2$ at the higher concentration than captured comes only from the entropy change of $H_2O$ which is applied to the sorbent. No external heat or pressure source is needed to concentrate atmospheric $CO_2$ by a factor of at least about 30 times, or at least about 40 times, or at least about 50 times, or at least about 60 times, or at least about 70 times, or at least about 80 times, or at least about 90 times, or at least about 100 times.

Treatment or Conversion of Photosynthetic Biomass after Growth and Collection

In some embodiments a system may comprise means of capturing $CO_2$ to grow photosynthetic biomass that may be collected then subjected to a method of treatment that transforms the photosynthetic biomass into a different usable product. A method of converting a photosynthetic biomass may comprise any of the preceding methods, devices, or systems for capturing and enriching $CO_2$ to facilitate growth of photosynthetic biomass. For example, steps for capturing and enriching $CO_2$ to facilitate growth of photosynthetic biomass may include: providing the photosynthetic biomass in an enclosure, capturing $CO_2$ from air that is exterior to the enclosure using one or more solid sorbents, and releasing the captured $CO_2$ from the sorbent into the enclosure. The captured $CO_2$ that is released into the enclosure may be used to grow of facilitate the growth of photosynthetic biomass, as such the $CO_2$ in the enclosure may be at a higher concentration than in the air exterior to the enclosure.

In some embodiments the photosynthetic biomass may be an aquatic macrophyte. An aquatic macrophyte may have a lignin content of at least 10%, at least 15%, at least 20%, or at least 30% of the dry mass of the aquatic macrophyte. An aquatic macrophyte may comprise at least one duckweed plant or at least one plant species from the *Azolla* genus. In some embodiments an aquatic macrophyte may comprise a mixture of at least one duckweed plant and at least one plant species from the *Azolla* genus, and at least one duckweed plant may be selected from the *Lemna* genus. In some embodiments at least one duckweed plant may be selected from the *Lemna* genus, and may be selected from a species that have a high concentration of elements and a low concentration of minerals compared to at least one other species of the *Lemna* genus.

The photosynthetic biomass may be collected before undergoing treatment or preparation steps, and the collection process may comprise harvesting the biomass by hand, use of heavy machinery including standard faming equipment, or use of a pond skimmer or similar device for collecting floating aquatic plants. After collection, photosynthetic biomass may be subjected to a variety of treatments.

Collected photosynthetic biomass may be subjected to thermal treatment. For example, the photosynthetic biomass may be collected and dried, then subjecting to thermal decomposition by heating. In some embodiments the photosynthetic biomass may be heated to a temperature sufficient to induce decomposition. Heating the photosynthetic biomass may results in pyrolysis of the photosynthetic biomass, in some embodiments pyrolysis may be slow pyrolysis, intermediate pyrolysis, or fast pyrolysis. The thermal decomposition of photosynthetic biomass may yield a solid phase composition. The solid phase composition may comprise char. The char may comprise at least 20%, at least 30%, at least 40%, or at least 45% of the dry weight of the photosynthetic biomass prior to being subjected to thermal decomposition. In some instances the conversion to char may be carbon negative or net energy positive. The char produced by the conversion may be biochar. A method for producing the char or biochar may comprise an addition step for collecting the char or bio char. The solid phase composition yielded by thermal treatment may be used as a fertilizer or be used to produce a fertilizer.

Collected photosynthetic biomass may also be subjected to digestions steps. Digestion may involve exposure of the photosynthetic biomass to a digester (e.g. anaerobic or aerobic digesters). Digesters may include anaerobic digesters, which subject the photosynthetic biomass to anaerobic digestions. An anaerobic digester may be designed to process organic waste into various usable products. These usable products may comprise methane, $CO_2$, and highly digestible inorganic nutrients. Usable products may be produced as a gas (e.g. effluent biogas) or a slurry (e.g. a digestate slurry). Gas products may be combusted to yield usable energy, and the resulting gaseous effluent may serve as a dilute-stream $CO_2$ source for agriculture. Effluent digestate and dilute-stream $CO_2$ may also be used in downstream processes. An anaerobic digester may be configured to provide $CO_2$ to a photosynthetic biomass growth chamber or growth tent. In some embodiments the $CO_2$ from an anaerobic digester may be configured to be the sole source of enriched $CO_2$, in other embodiments the system may be configured to include other $CO_2$ sources including ambient air. Configuring the system may comprise adjusting the size of the anaerobic digester based on the digestate (e.g. components in the digestate including nutrients) and power demands. The anaerobic digestions systems may yield biogas, wherein the biogas is a mixture of methane and $CO_2$. In some embodiments the biogas mixture may comprise greater than or equal to 50%, greater than or equal to 60%, greater than or equal to 70% of methane gas. Is further embodiments the biogas mixture may comprise greater than or equal to 40%, greater than or equal to 50%, or greater than or equal to 60% of $CO_2$ gas. Biogas may be combusted through a cogeneration unit to provide power for the facility and vent off agriculture grade $CO_2$.

Collected photosynthetic biomass may also be subjected to treatment in a bioreactor or in a facility for producing ethanol. In some cases, ethanol production may comprise exposure of the photosynthetic biomass to enzymes. Enzymes, for example amylase, may convert starch found in the photosyntehtic biomass into sugars. The sugars that are formed may undergo subsequent fermentation steps. Fermentation may be performed by yeast, and the process may yield transportation grade bio-ethanol. The fermentation process may also yield concentrated $CO_2$. Concentrated $CO_2$ may be mineralized and geologically sequestered. Post-process yeast may subsequently be disposed of in an anaerobic digester.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Agricultural Runoff Purification with Duckweed

Duckweed is grown in five layered, shallow, rectangular enclosures, wherein each layer is vertically arranged in step-wise tiers, each approximately 1 meter in depth. Agricultural runoff flows into the enclosure creating or sustaining a depth of 6-8 inches of water, with the duckweed suspended in the contained water, making contact with and removing contaminants from the water as it flows through the layers before flowing out of the enclosure. The enclosure is configured such that the duckweed can grow using natural sunlight alone, or is outfitted with LED lights that are powered by a single or combined power sources selected from solar panels, pinwheel wind generators or other alternative energy sources. To enhance the growth of duckweed by delivery of $CO_2$, a $CO_2$ sorbent formed in a matrix is configured as a rotating wheel that rotates from inside the enclosure to outside the enclosure. Rotation of the sorbent matrix enables $CO_2$ to be transferred from the enclosure using humidity swings. The sorbent surface first captures the $CO_2$ from outside the enclosure, then releases the $CO_2$ into the enclosure, thereby regenerating the sorbent surface for repeated rounds of $CO_2$ capture, $CO_2$ transfer and sorbent regeneration. The enclosure is connected with at least one such sorbent wheel. The enclosure may be connected to one sorbent wheel for each layer of the enclosure. The sorbent wheel rotates, exposing sorbent surface to an arid external environment from which the sorbent captures $CO_2$. Rotation of the wheel also exposes surfaces previously exposed to the external environment to air from the enclosure. Within the enclosure, the wheel is exposed to air of higher humidity or is placed in fluid contact with the water held within the enclosure. Once in the enclosure, the water or humidity of the enclosure induces release of $CO_2$ from the sorbent into the enclosure, thus regenerating the sorbent and providing $CO_2$ to the duckweed, which grows more quickly as a result of the higher levels of $CO_2$. As the wheel rotates, the process of $CO_2$ capture and release continues at the sorbent surfaces exposed to air from outside and inside the enclosure, respectively. The duckweed is harvested from the enclosures using a vacuum method which sucks the duckweed into a collection unit. Harvest of the duckweed occurs continuously, with the harvests removed from the enclosure and subjected to further processing on-site. The duckweed undergoes several rounds of processing. First, oil is pressed out of the collected duckweed for use in the production of biodiesel. The remaining high-protein duckweed biomass is used for animal feed, either directly or by a process in which protein components are removed from the biomass, dried and mixed with other biofeed components (such as soy meal, corn meal or fish meal). Finally, any additional residual biomass is refined to extract fixed nitrogen, phosphorous or other nutrients for fertilizer production.

Example 2: Regulation of Indoor $CO_2$ by Absorption and Delivery to a Greenhouse Duckweed is grown within a 4×4 growth tent in the basement of a building as shown in FIG. 3. A carbon purification system may be installed in an indoor living or working space. To reduce high concentrations of $CO_2$ a system is provided comprising a sorbent for capturing $CO_2$ and transferring it to a 4×4 growth tent for growing duckweed. The sorbent surface may first capture the $CO_2$, then transfer it through the HVAC system to the growth tent where the $CO_2$ is consumed by the duckweed. The growth tent may comprise water, light, nutrients, pumps, filters and other components for growing duckweed indoors. The sorbent may be installed into one or more compartments including rooms or floors where $CO_2$ is captured and transferred through the HVAC system to the basement of the building. When the system is operating, the $CO_2$ concentration in the one or more compartments may be about 405 ppm and the concentration in the growth tent may be about 650 ppm.

Example 3: Method and System for $CO_2$ Sequestration and Ethanol Production

A fully integrated, self-powering, and substantially carbon neutral system is provided comprising a greenhouse have a $CO_2$ sequestering device in accordance with an embodiment of the disclosure, a bio-ethanol fermentation unit, an anaerobic digester and a methane combustion unit. A $CO_2$ sequestering device in accordance with an embodiment of the disclosure is configured to capture $CO_2$ from outdoor ambient air and deliver it to the interior of a greenhouse. The greenhouse contains growing duckweed of the genus *Lemna*. The device raises $CO_2$ concentration in the greenhouse above that of the outdoor ambient air, with a corresponding increase in *Lemna* biomass production. Preferably, the species of *Lemna* selected for the greenhouse is one that grows rapidly, is native to the region in which the greenhouse is situated, and contains high amounts of starch. The *Lemna* are cultivated in shallow pools within the greenhouse. Environmental conditions are controlled, such as temperature, humidity, $CO_2$, and/or light exposure. As the *Lemna* grows, it is harvested automatically based on specified parameters. *Lemna* growth also reduces water contamination, such that the greenhouse may serve as a step in a water treatment process to generate cleaner water.

Harvested *Lemna* is used as a feedstock in the production of bio-ethanol in a fermentation unit. In this process, starch is separated from other *Lemna* components, such as proteins and lipids. The proteins and lipids may be used as feedstocks in other processes. The starch is converted into sugars through saccarification, such as by using amylase. Sugars are fermented by yeast to yield transportation-grade bio-ethanol. The fermentation process also produces concentrated $CO_2$. The concentrated $CO_2$ is fed into the greenhouse, supplied as a feedstock to another process, or physically sequestered (e.g. geological injection). Once used in the fermentation process, yeast are disposed of in an anaerobic digester.

In addition to the greenhouse, $CO_2$ sequestering device, and fermentation unit, the system of this example also includes an anaerobic digester. Disposable material, such as yeast used in the fermentation unit, is used as a feedstock in the digester. The disposable material may include other feedstocks, such as manure and/or other organic waste. Anaerobic digestion of the disposable materials produces biogas (which is about 60% methane, and 40% $CO_2$), and inorganic nutrients (e.g. nitrogen, phosphate, and potassium). The nutrients are provided to the *Lemna* to support growth in the greenhouse. The methane is combusted to generate electricity for operating the system, and any excess electricity is supplied to the grid. $CO_2$ produced by the digester and by methane combustion are also fed into the greenhouse to supplement the $CO_2$ from the sequestering device. Excess $CO_2$ is supplied as a purified feedstock for use in other processes, or is physically sequestered (e.g. geological injection).

The self-powering system is substantially carbon neutral, and provides a source of useful products, including concentrated $CO_2$, electricity, and bio-ethanol. The bio-ethanol is provided as a gasoline supplement. In operation, the system processes about 2200 pounds of volatile solids (e.g. manure) per day, and produces 2 cubic meters of biogas per square meter of digester per day. This yields approximately 200 kWh of power per day. The system produces about or more than about 250 tons/ha/year dry weight of *Lemna*, and 71 tons/ha/year of ethanol.

Example 4: Ethanol Production Facility

An ethanol production facility is provided in a desert. The facility is designed grow *Lemna* and to convert the *Lemna* into ethanol. A high-starch yielding species of *Lemna* is grown at the facility. *Lemna* starch is highly digestible by yeast, therefore high starch-to-ethanol conversion rates are achieved through basic ethanol production practices. The facility includes a *Lemna* growth facility and an ethanol production facility. The *Lemna* growth facility spans 713 hectares (1,783 acres) and includes a series of sealed growth tents wherein the *Lemna* is grown. Each growth tent includes an amine sorbent wheel that is positioned such that as the wheel rotates the sorbent alternates between communication with the exterior ambient air and communication with the tent's sealed interior air. As the sorbent communicates with the exterior ambient air it absorbs $CO_2$ from the atmosphere. The relative humidity inside the tent is maintained at least 40%, at least 50%, at least 60%, at least 70%, at least 80%. As the sorbent communicates with the humid interior air, $CO_2$ is released therefrom. The *Lemna* is periodically harvested and used as the feedstock for the ethanol production in the ethanol production facility. The facility produces 157,560 tons of sequesterable $CO_2$ per year. By displacing the equivalent level of fossil fuel combustion, this ethanol product mitigates the release of 500,190 tons of $CO_2$ per year.

Example 5: Smaller Scale Greenhouse

Systems are provided for smaller scale indoor, rooftop, and small scale duckweed cultivation. The system ranging from 5 feet to 50 feet in length and width, 5 feet to 15 feet in height, will generate 1500 ppm $CO_2$ for 25 to 750 square feet of greenhouse space each hour using no more energy than what is needed to power two small fans.

Example 6: Larger-Scale Greenhouse

Systems are provided for larger scale indoor cultivators, rural greenhouse growers, and large scale indoor urban grower. The larger scale system serves one acre or more with $CO_2$, and enables consistent concentrations of 1200 to 1500 ppm $CO_2$.

Example 7: Modular Greenhouse

Modular greenhouse systems are provided for duckweed production. Modular Greenhouses are optimized to contain $CO_2$ and have reduced overhead costs. The design incorporates large, interconnected production channels installed on flat, non-arable, land and covered with transparent plastic sheets to retain $CO_2$ and moisture. The channels are "raceways" optimized for duckweed growth. Water volume used in production is small. Each modular production system has a low profile and is tightly sealed to diminish loss of $CO_2$, heat, and moisture, and associated costs.

The system utilizes an automated extraction system and $CO_2$ monitoring and air-circulation equipment. Little to no system maintenance is necessary. Duckweed is harvested from the end of the raceway utilizing a paddle to pull the mat along. Duckweed pulled from the beginning of the channel creates a void in which young duckweed clones spread into and occupy within hours. Continual extraction prevents the mat from becoming too thick, which would slow growth. Continual extraction enables optimal duckweed growth rates.

Example 8: Pond Greenhouse

A pond greenhouse is provided, wherein *Lemna* production channels in an open pond are enclosed with growth tents having amine sorbent wheels as described in Example 4. The humidity within the tents is maintained at a minimum humidity of at least 40%, at least 50%, at least 60%, at least 70%, at least 80%. The sorbent wheels are operated to maintain the $CO_2$ content within the tents at a minimum of 1500 ppm. At 1500 ppm, the *Lemna* growth rate is increased by 4× as compared to its growth rate in an air environment containing only 400 ppm $CO_2$. A biomass production rate of 400 tons per hectare per year of *Lemna* that is of 60% starch is achieved. The 400 tons per hectare per year of *Lemna* is used to produce 70,153 gallons of ethanol per hectare of land.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the inventions of the present disclosure, and that each of the various individual aspects of the invention described herein may be combined or interchanged in any manner even if such combination of aspects is not specifically described herein. It is intended that the following claims define the scope of the invention and that methods and structures within the scope of these claims and their equivalents be covered thereby.

What is claimed is:

1. A system for capturing $CO_2$ from an atmosphere and treating water, the system comprising: (a) an enclosure having an interior comprising aquatic macrophytes; (b) a water inlet opening in the enclosure configured to allow contaminated water to enter the enclosure and contact the aquatic macrophytes; and (c) a solid sorbent configured to capture $CO_2$ in air exterior to the enclosure and release the captured $CO_2$ to the interior of the enclosure.

2. The system of claim 1, wherein the aquatic macrophytes comprise *Eichhornia, Spirodela, Salvinia, Azolla, Lemna, Pistia*, heartleaf, duckweed, or members of the duckweed family.

3. The system of claim 1, wherein the enclosure comprises a plurality of vertically arranged tiers comprising the aquatic macrophytes.

4. The system of claim 3, wherein each tier is in fluid communication with a separate solid sorbent.

5. The system of claim 1, further comprising an artificial light source configured to provide light to the aquatic macrophytes.

6. The system of claim 1, further comprising a passive power source selected from the group consisting of a solar panel, a wind turbine, a hydroelectric generator, and a thermal energy converter.

7. The system of claim 1, wherein the contaminated water is a lake, a pond, a stream, a river, a canal, agricultural runoff, or a reservoir.

8. The system of claim 1, wherein the contaminant is a nitrogen-containing compound comprising a nitrate, nitrite, or ammonium.

9. The system of claim 1, wherein the solid sorbent comprises an anion exchange material.

10. The system of claim 1, further comprising a moisture control apparatus configured to expose the solid sorbent to increased moisture that facilitates the release of $CO_2$ therefrom; wherein the moisture control apparatus comprises either (1) a controlled water inlet configured to bring a controlled amount of water into contact with the solid sorbent, or (2) a humidifier; and wherein the moisture control apparatus is configured to expose the solid sorbent to $H_2O$ that is a gas, solid, or liquid.

11. The system of claim 1, wherein the solid sorbent comprises a sorbent material distributed on or in a support material.

12. The system of claim 1, wherein (i) the solid sorbent is distributed about an axis around which the sorbent rotates; (ii) the sorbent comprises a first surface and a second surface; and (iii) the solid sorbent is positioned relative to the enclosure such that as the sorbent rotates about the axis at least a portion of the first surface enters the enclosure and at least a portion of the second surface exits the enclosure.

13. A method of capturing $CO_2$ from atmosphere and treating water, the method comprising: (a) introducing water comprising a contaminant into an enclosure having an interior containing an aquatic macrophyte such that the water comes into contact with the aquatic macrophyte, and wherein the aquatic macrophyte facilitates reduction of the level of the contaminant in the water; (b) capturing $CO_2$ from air exterior to the enclosure with a solid sorbent; and (c) releasing captured $CO_2$ into the interior of the enclosure, wherein the interior of the enclosure has a higher $CO_2$ concentration than the air exterior to the enclosure.

14. The method of claim 13, wherein the aquatic macrophyte comprises *Eichhornia, Spirodela, Salvinia, Azolla, Lemna, Pistia*, heartleaf, duckweed, or members of the duckweed family.

15. The method of claim 13, wherein the air exterior to the enclosure is outdoor atmospheric air.

16. The method of claim 13, wherein the contaminant is a nitrogen-containing compound comprising a nitrate, nitrite, or ammonium.

17. The method of claim 13, wherein the solid sorbent comprises an anion exchange material.

18. The method of claim 13, wherein the step of releasing captured $CO_2$ comprises wetting the sorbent or exposing the sorbent to increased humidity.

19. The method of claim 13, wherein the solid sorbent comprises a sorbent material distributed on or in a support material.

20. The method of claim 13, wherein (i) the solid sorbent is distributed about an axis around which the sorbent rotates, (ii) the sorbent comprises a first surface and a second surface, and (iii) the solid sorbent is positioned relative to the enclosure such that as the sorbent rotates about the axis at least a portion of the first surface enters the enclosure and at least a portion of the second surface exits the enclosure; and wherein the method further comprises rotating the sorbent about the axis to alternate exposing the first surface and the second surface to the exterior of the enclosure.

21. The method of claim 13, wherein the contaminant in treated water exiting the enclosure has a concentration that is at least 10% lower as compared to water entering the enclosure.

22. The method of claim 13, further comprising the step of maintaining the $CO_2$ concentration in the interior of the enclosure at a level at which duckweed exhibits a growth rate or reproduction rate that is at least 2-fold increased as compared to growth or reproduction of duckweed in the air exterior to the enclosure.

23. The method of claim 22, wherein the $CO_2$ concentration is maintained for at least 2 days.

24. The method of claim 13, further comprising the step of maintaining the $CO_2$ concentration in the interior of the enclosure at least 1000 ppm, 1200 ppm, 1500 ppm, or higher.

* * * * *